(12) United States Patent
Schmidt et al.

(10) Patent No.: US 8,445,511 B2
(45) Date of Patent: May 21, 2013

(54) QUINOLINE OR QUINOXALINE DERIVATIVES FOR TREATING NEURODEGENERATIVE DISEASES

(75) Inventors: Fanny Schmidt, Chatenay Malabry (FR); Bruno Figadere, Saint Cheron (FR); Sylvia Rita Vozari, Paris (FR); Pierre Champy, Palaiseau (FR); Xavier Franck, Bois Guillaume (FR)

(73) Assignee: Centre National de la Recherche Scientifique (SNRS), Paris (FR)

( * ) Notice: Subject to any disclaimer, the term of this patent is extended or adjusted under 35 U.S.C. 154(b) by 113 days.

(21) Appl. No.: 13/003,992

(22) PCT Filed: Jul. 20, 2009

(86) PCT No.: PCT/EP2009/059285
§ 371 (c)(1),
(2), (4) Date: Jan. 13, 2011

(87) PCT Pub. No.: WO2010/007179
PCT Pub. Date: Jan. 21, 2010

(65) Prior Publication Data
US 2011/0118270 A1 May 19, 2011

(30) Foreign Application Priority Data
Jul. 18, 2008 (FR) ...................................... 08 54921

(51) Int. Cl.
*A61K 31/47* (2006.01)
(52) U.S. Cl.
USPC .......................................... 514/311; 546/181
(58) Field of Classification Search
USPC .......................................... 514/311; 546/181
See application file for complete search history.

(56) References Cited

U.S. PATENT DOCUMENTS

| | | | |
|---|---|---|---|
| 7,342,026 B2 * | 3/2008 | Fakhfakh et al. | 514/312 |
| 2005/0234064 A1 | 10/2005 | Bemis et al. | |
| 2005/0272736 A1 | 12/2005 | Altenbach et al. | |

FOREIGN PATENT DOCUMENTS

| | | |
|---|---|---|
| CN | 1966500 A | 5/2007 |
| EP | 0 317 188 B1 | 9/1995 |
| EP | 0 640 676 B1 | 1/1999 |
| EP | 0 622 359 B1 | 3/2003 |
| EP | 1 054 863 B1 | 5/2003 |
| EP | 1 854 487 A2 | 11/2007 |
| EP | 1 186 594 B1 | 8/2009 |
| JP | 8-209135 | 8/1996 |
| WO | WO 02/18341 A2 | 3/2002 |
| WO | WO 2004/031161 A1 | 4/2004 |
| WO | WO 2005/066132 A1 | 7/2005 |
| WO | WO 2006/108666 A1 | 10/2006 |

OTHER PUBLICATIONS

Fakhfakh, et al. Bioorganic & Medicinal Chemistry, 11(23), 2003, 5013-5023.*
International Search Report issued in application No. PCT/EP2009/059285 on Dec. 9, 2009.
Hui et al., "Synthesis and antiprotozoal activity of some new synthetic substituted quinoxalines," Bioorganic & Medicinal Chemistry Letters, vol. 16, pp. 815-820, 2006.
Lipshutz et al., "Nickel(0)-Catalyzed Couplings of Vinyl-Alanes &-Zirconocenes with Chloromethylated Heteroaromatics: A Route to E-Allylated Heterocycles," Tetrahedron, vol. 54, pp. 6999-7012, 1998.
Fakhfakh et al., "Expeditious preparation of 2-substituted quinolines," Tetrahedron Letters, vol. 42, pp. 3847-3850, 2001.
Buu-Hoï et al., "Sur l'utilisation de la reaction de Pfitzinger pour la synthése des alkyl-2 quinoléines à longue chaîne," Mémoires Soc. Chim., pp. 1567-1569, 1958.
Gautier et al., "Accès aux quinoléines à fonctions multiples à partir des quinolylalcynes monosubstitués," Mémoires Soc. Chim., pp. 2098-2109, 1961.
Renault et al., "Aminoquinolénes secondaires à activité amoebicide potentielle: influence de la longueur et de la position de la chaîne alkylaminée," C.R. Acad. Sc. Paris, vol. 282, pp. 509-511, 1976.

* cited by examiner

*Primary Examiner* — Douglas M Willis
(74) *Attorney, Agent, or Firm* — Foley & Lardner LLP

(57) ABSTRACT

The present invention relates to compounds of Formula (I) below, to their pharmaceutically acceptable salts and to their isomers or mixtures of isomers: HetAr—X—CHR$^1$R$^2$ (I) in which: —HetAr represents a group chosen from: —X represents a linear, saturated or unsaturated, hydrocarbon-based chain comprising from 8 to 22 carbon atoms, optionally interrupted by an —NH— or —NH—CO— group, —R$^1$ represents a hydrogen atom or an —OH, —O(C$_1$-C$_6$)alkyl, —OCO((C$_1$-C$_6$)alkyl), —OSO$_2$((C$_1$-C$_6$)alkyl) or —OSO$_3$H group, and —R$^2$ represents a hydrogen atom or a (C$_2$-C$_6$) alkynyl, (C$_2$-C$_6$)alkenyl or (C$_3$-C$_6$)cycloalkyl group. The present invention also relates to a process for preparing the compounds of Formula (I), and also to the use thereof, especially in the treatment of neurodegenerative diseases.

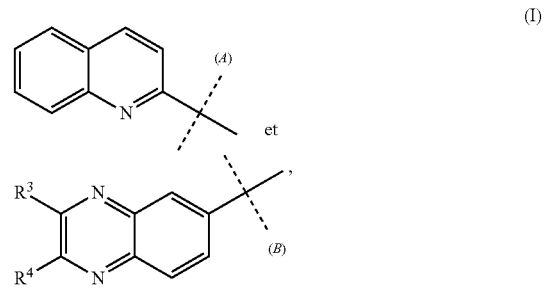

20 Claims, 3 Drawing Sheets

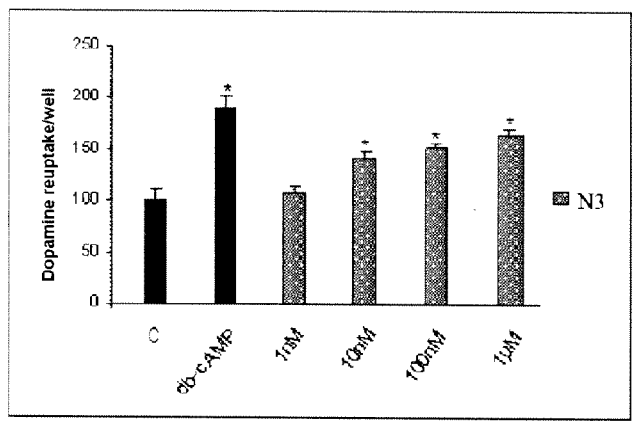
Figure 4
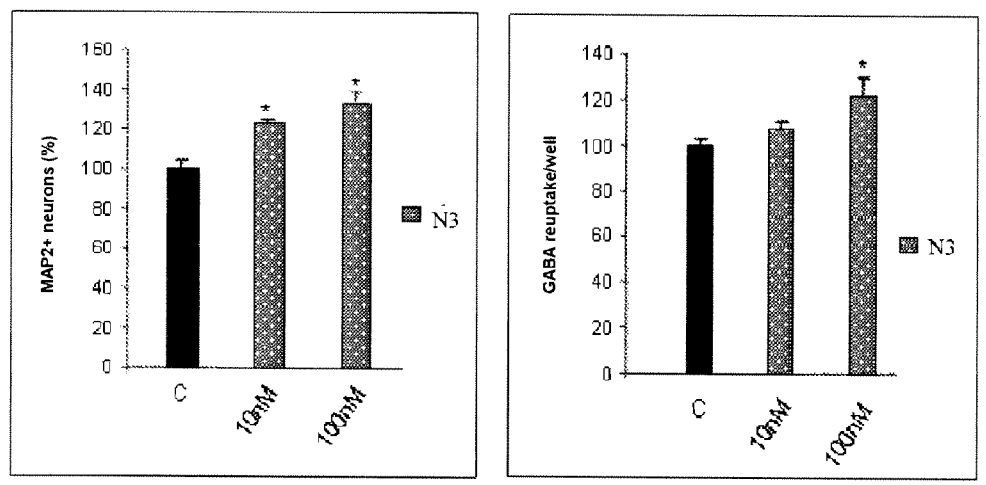
Figure 5
Figure 6

QUINOLINE OR QUINOXALINE DERIVATIVES FOR TREATING NEURODEGENERATIVE DISEASES

CROSS-REFERENCE TO RELATED PATENT APPLICATIONS

France Priority Application 0854921, filed Jul. 18, 2008 including the specification, drawings, claims and abstract, is incorporated herein by reference in its entirety.

BACKGROUND OF THE INVENTION

1. Field of the Invention

The present invention relates to chimeric compounds having a quinoline or quinoxaline motif substituted by an aliphatic chain useful in the treatment of neurodegenerative diseases, and to a method for preparing same and to the use of same.

2. Description of Related Art

With longer life expectancies, more and more people are suffering from neurodegenerative diseases such as Alzheimer's disease or Parkinson's disease.

A neurodegenerative disease is a disease that affects the functioning of the nervous system, in particular the brain, in a progressive manner. The disease can develop more or less rapidly (several weeks to several years), and is often irreversible. Thus, the functioning of nerve cells, in particular neurons, deteriorates, which can lead to cell death. Depending on the region of the nervous system affected by the disease, various functions could be affected such as motor skills, language, memory, perception or cognition. The most common neurodegenerative diseases include in particular Alzheimer's disease and Parkinson's disease.

Alzheimer's disease, which affects roughly 24 million people worldwide, is a disease of the cerebral tissue that leads to the progressive and irreversible loss of mental functions. The first symptom is the loss of memory of recent events (amnesia), followed by cognitive deficits extending to the areas of language (aphasia), organization of movements (apraxia), visual recognition (agnosia) and executive functions (such as decision making and planning).

Parkinson's disease affects the central nervous system and causes progressively-evolving motor disorders, notably tremors of the body.

Currently, the drugs prescribed for these two diseases are only effective in delaying the progress of the disease. None cure the disease, nor stop its progress, which is why there is a need to find new, more active molecules to treat these neurodegenerative diseases.

SUMMARY OF THE INVENTION

The present invention thus relates to a compound of formula (I) as follows:

$$\text{HetAr—X—CH}^1\text{R}^2 \qquad (I)$$

wherein:

HetAr represents a group selected from:

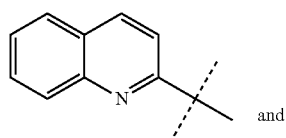

and

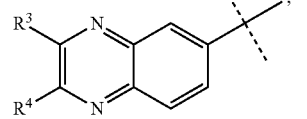

with $R^3$ and $R^4$ representing, independently of each other, a hydrogen atom, a saturated or unsaturated, linear or branched hydrocarbon chain, comprising from 1 to 6 hydrogen atoms or an aryl group, $R^3$ preferably representing a hydrogen atom, X represents a linear, saturated or unsaturated hydrocarbon chain comprising from 8 to 22 carbon atoms, preferably from 10 to 16 carbon atoms, and optionally interrupted by an —NH— or —NH—CO— group, said group being preferably directly linked to HetAr, $R^1$ represents a hydrogen atom or an $OR^5$ group, with $R^5$ representing a hydrogen atom or an $R^{5a}$ group selected from $(C_1-C_6)$ alkyl, —CO$((C_1-C_6\text{alkyl}))$, —SO$_2((C_1-C_6)\text{alkyl})$ and —SO$_3$H, and $R^2$ represents a hydrogen atom or an $R^{2a}$ group selected from a $(C_2-C_6)$alkynyl, $(C_2-C_6)$alkenyl or $(C_3-C_6)$cycloalkyl group, as well as the pharmaceutically acceptable salts of same, the isomers or mixtures of isomers in all proportions of same, in particular a mixture of enantiomers, and notably a racemic mixture.

DETAILED DESCRIPTION OF THE INVENTION

"$(C_1-C_6)$-alkyl" group means, in the context of the present invention, a saturated, linear or branched hydrocarbon chain, comprising from 1 to 6 carbon atoms, in particular the following groups: methyl, ethyl, n-propyl, isopropyl, n-butyl, iso-butyl, sec-butyl, tert-butyl, n-pentyl and n-hexyl.

"$(C_2-C_6)$-alkenyl" group means, in the context of the present invention, a linear or branched hydrocarbon chain comprising at least one double bond and comprising from 2 to 6 carbon atoms, such as for example a vinyl or allyl group, preferably a vinyl group.

"$(C_2-C_6)$-alkynyl" group means, in the context of the present invention, a linear or branched hydrocarbon chain comprising at least one triple bond and comprising from 2 to 6 carbon atoms, such as for example an ethynyl or propynyl group, preferably an ethynyl group.

"$(C_3-C_6)$-cycloalkyl" group means, in the context of the present invention, a saturated hydrocarbon ring comprising from 3 to 6 carbon atoms, in particular a cyclohexyl, cyclopentyl or cyclopropyl group, advantageously a cyclopropyl group.

"Aryl" group means, in the context of the present invention, an aromatic group comprising preferably from 5 to 10 carbon atoms and comprising one or more joined rings, such as for example a phenyl or naphthyl group, advantageously a phenyl group.

"Unsaturated" means, in the context of the present invention, that the hydrocarbon chain can comprise one or more unsaturations.

"Unsaturation" means, in the context of the present invention, a double or triple bond.

In the present invention, "pharmaceutically acceptable" means what is useful in the preparation of a pharmaceutical composition that is generally safe, nontoxic and neither biologically nor otherwise undesirable and that is acceptable for veterinary or human pharmaceutical use.

"Pharmaceutically acceptable salts" of a compound means, in the context of the present invention, salts that are pharmaceutically acceptable, as defined herein, and that have the desired pharmacological activity of the parent compound. Such salts include:

(1) hydrates and solvates, (2) acid addition salts formed with inorganic acids such as hydrochloric acid, hydrobromic acid, sulfuric acid, nitric acid, phosphoric acid and similar; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2 naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and similar; and (3) salts formed when an acid proton present in the parent compound is either replaced by a metal ion, for example an alkaline metal ion ($Na^+$, $K^+$ or $Li^+$ for example), an alkaline-earth metal ion (such as $Ca^{2+}$ or $Mg^{2+}$) or an aluminum ion; or coordinates with an organic or inorganic base. Acceptable organic bases include diethanolamine, ethanolamine, N-methylglucamine, triethanolamine, tromethamine and similar. Acceptable inorganic bases include aluminum hydroxide, calcium hydroxide, potassium hydroxide, sodium carbonate and sodium hydroxide.

"Isomers" means, in the context of the present invention, diastereoisomers or enantiomers. They are thus optical isomers, also called "stereoisomers". Stereoisomers that are not mirror images of one other are thus called diastereoisomers, and stereoisomers that are not superimposable mirror images are called enantiomers.

A carbon atom linked to four nonidentical substituents is called a "chiral center".

An equimolar mixture of two enantiomers is called a racemic mixture.

According to a first particular embodiment of the invention, HetAr represents

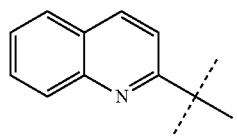

and X represents an X1 chain which is a saturated linear hydrocarbon chain or an unsaturated linear hydrocarbon chain comprising at least one triple bond or one double bond, preferably one triple bond, directly linked to HetAr, said chain comprising from 8 to 22 carbon atoms, preferably from 10 to 16 carbon atoms.

Advantageously, when X1 represents an unsaturated hydrocarbon chain, X1 will comprise only one unsaturation, namely the double or triple bond, and preferably the triple bond, directly linked to HetAr.

According to a second particular embodiment of the invention, HetAr represents

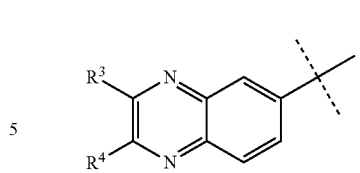

and $R^3$ and $R^4$ are as defined above, and X represents an —NH—X2- or —NH—CO—X2- group, where NH is directly linked to HetAr and X2 represents a linear, saturated or unsaturated hydrocarbon chain comprising from 8 to 22 carbon atoms, preferably from 10 to 16 carbon atoms.

Preferably, $R^3$ represents a hydrogen atom and $R^4$ represents a ($C_1$-$C_6$) alkyl or aryl group, advantageously a ($C_1$-$C_6$) alkyl group.

According to another particular embodiment of the invention, $R^1$ represents a hydrogen atom and $R^2$ represents a hydrogen atom.

According to still another particular embodiment of the invention, $R^1$ represents an $OR^5$ group, and $R^2$ represents a hydrogen atom or an $R^{2a}$ group selected from a ($C_2$-$C_6$)alkynyl, ($C_2$-$C_6$) alkenyl or ($C_3$-$C_6$)cycloalkyl group.

Advantageously, $R^1$ and $R^2$ each represent a hydrogen atom or $R^1$ represents an OH group and $R^2$ represents a ($C_2$-$C_6$)alkynyl group such as —C≡CH, a ($C_2$-$C_6$)alkenyl group such as —CH=$CH_2$— or a ($C_3$-$C_6$cycloalkyl group such as —$C_3H_5$, and preferably represents a —C≡CH group.

In particular, the compounds of the invention can be selected from:

F1

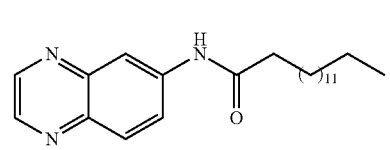

F2

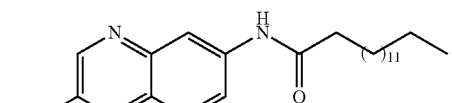

F3

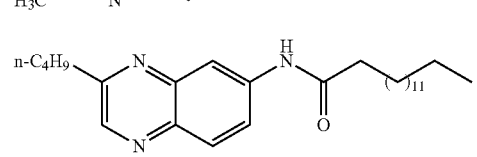

F4

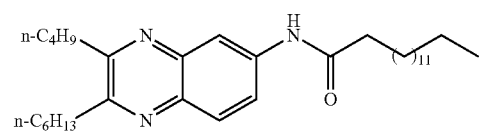

G1

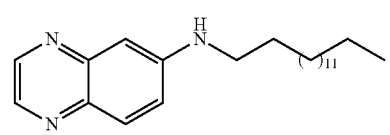

G2

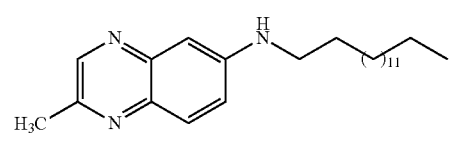

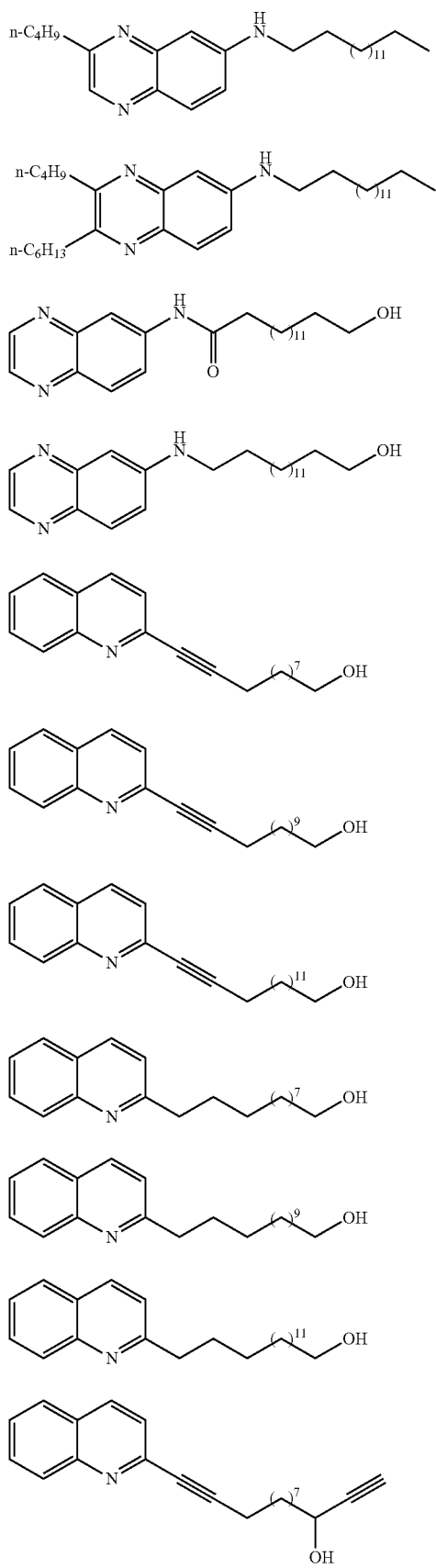
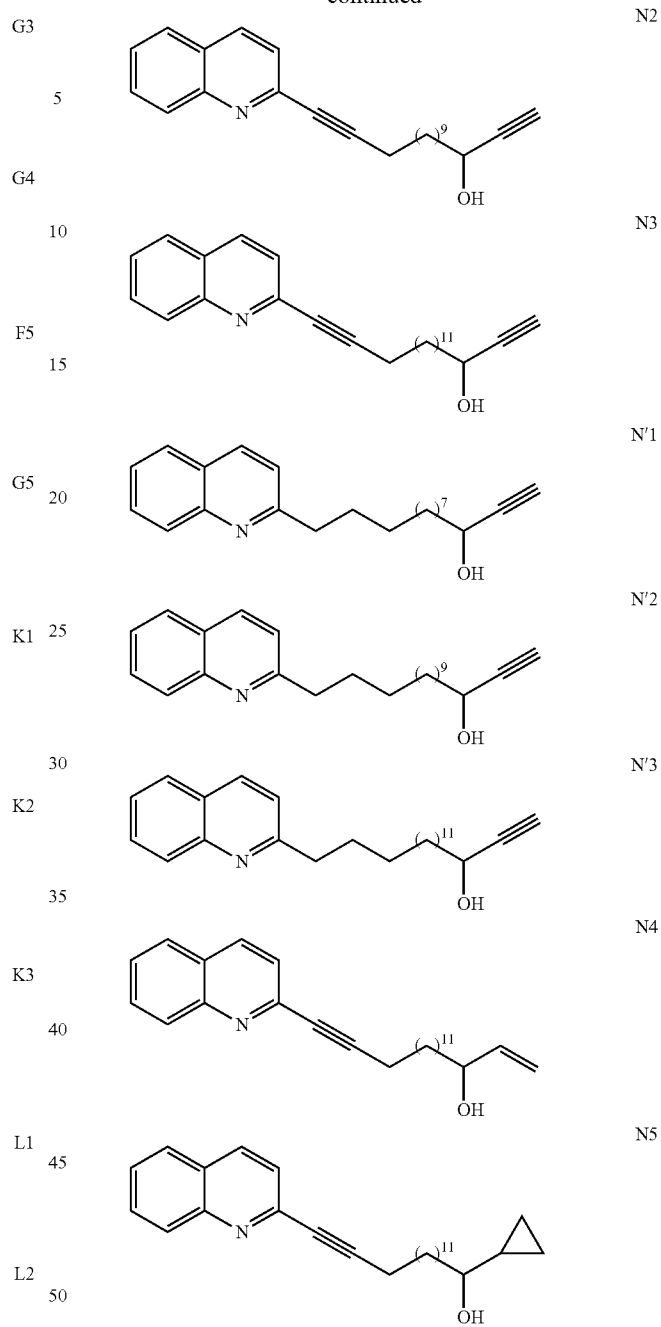

The present invention also relates to a compound of the invention as defined above, for the use of same as a drug, notably as a neurotrophic or neuroprotective drug, advantageously to treat or prevent neurodegenerative diseases such as Alzheimer's disease, Parkinson's disease, multiple sclerosis or cerebral vascular accidents.

The present invention also relates to the use of a compound of the invention as defined above to manufacture a neurotrophic or neuroprotective drug, advantageously to treat or prevent neurodegenerative diseases such as Alzheimer's disease, Parkinson's disease, multiple sclerosis or cerebral vascular accidents.

The present invention also relates to a method of treatment or prevention of neurodegenerative diseases such as Alzheimer's disease, Parkinson's disease, multiple sclerosis or cerebral vascular accidents, comprising the administration of a sufficient quantity of a compound of the invention to a patient in need.

The present invention also relates to a pharmaceutical composition comprising at least one compound of the invention as defined above and a pharmaceutically acceptable carrier.

The compounds of the invention can be administered by oral, sublingual, parenteral, subcutaneous, intramuscular, intravenous, transdermal, local or rectal route.

In the pharmaceutical compositions of the present invention for oral, sublingual, parenteral, subcutaneous, intramuscular, intravenous, transdermal, local or rectal administration, the active ingredient can be administered in unit dosage forms, in mixture with traditional pharmaceutical carriers, to animals or humans. Suitable unit dosage forms comprise forms by oral route such as tablets, gelatine capsules, powders, granules and oral solutions or suspensions; sublingual and oral administration forms; parenteral, subcutaneous, intramuscular, intravenous, intranasal or intraocular administration forms; and forms for rectal administration.

When a solid composition in tablet form is prepared, the principal active ingredient is mixed with a pharmaceutical carrier such as gelatine, starch, lactose, magnesium stearate, talc, gum arabic or analogs. Tablets can be coated with saccharose or other suitable materials or can be treated in such a way that they have extended or delayed activity and that they continuously release a predetermined quantity of active ingredient.

A preparation in gelatine capsules is obtained by mixing the active ingredient with a diluent and by pouring the mixture obtained into soft or hard gelatine capsules.

A preparation in syrup or elixir form can contain the active ingredient together with a sweetener, an antiseptic, as well as a flavouring agent and a suitable colorant.

Water-dispersible powders or granules can contain the active ingredient in mixture with dispersion or wetting agents, or suspension agents, as well as with flavour correctors or sweeteners.

For rectal administration, suppositories that are prepared with binders that melt at rectal temperature, for example cocoa butter or polyethylenes glycols, are used.

For parenteral, intranasal or intraocular administration, aqueous suspensions, isotonic saline solutions or sterile and injectable solutions that contain pharmacologically compatible dispersants and/or wetting agents are used.

The active ingredient can also be formulated in the form of microcapsules, optionally with one or more additives.

The compounds of the invention can be used in doses between 0.01 mg and 1,000 mg per day, and can be given in a single dose once per day or can be administered in several doses throughout the day, for example twice a day in equal doses. The daily dose administered is advantageously between 5 mg and 500 mg, even more advantageously between 10 mg and 200 mg. It may be necessary to use doses beyond these ranges according to the experience of the person skilled in the art.

According to a particular embodiment, the pharmaceutical composition as defined above may further include another active ingredient, useful notably to treat or prevent neurodegenerative diseases, and advantageously selected from acetylcholinesterase inhibitors such as donepezil, galantamine, rivastigmine, memantine and tacrine; monoamine oxidase inhibitors such as selegiline; catechol-O-methyltransferase inhibitors such as entacapone; glutamatergic inhibitors such as amantadine and baclofen; cholinergic agonists such as sabcomeline; dopaminergic agonists such as pergolide, cabergoline, ropinirole and pramipexole; neurotransmitter analogs or precursors such as L-3,4-dihydroxyphenylalanine; and anticholinergics such as trihexyphenidyl and tropatepine.

The present invention also relates to a method for preparing a compound of formula (I) as defined above wherein $R^1$ represents an $OR^5$ group as defined above and $R^2$ represents an $R^{2a}$ group as defined above, wherein it comprises the following steps:

bringing together a compound of formula (II) as follows:

HetAr—X—CHO  (II)

wherein HetAr and X are as previously defined, with a compound of formula $R^{2b}$-M, wherein $R^{2b}$ represents an $R^{2a}$ group as previously defined, optionally in a protected form, and M represents an alkaline metal such as lithium or an alkaline-earth metal linked to a halogen atom such as a bromo or chloro magnesium, to yield a compound of formula (III) as follows:

HetAr—X—CH(OH)$R^{2b}$  (III)

wherein HetAr and X are as previously defined, and $R^{2b}$ is as defined above, optionally a step of deprotection of the $R^{2b}$ group to yield the $R^{2a}$ group in deprotected form, as defined above, leading to a compound of formula (Ia) as follows:

HetAr—X—CH(OH)$R^{2a}$  (Ia)

wherein HetAr, $R^{2a}$ and X are as previously defined, optionally a step of substitution of the OH group of the compound of formula (Ia) obtained in the preceding step to yield a compound of formula (Ib) as follows:

HetAr—X—CH(OR$^{5a}$)$R^{2a}$  (Ib)

wherein HetAr, $R^{5a}$, $R^{2a}$ and X are as defined previously, and recovery of compound (I) obtained in the preceding step and corresponding to compound (III), (Ia) or (Ib).

"Alkaline metal" means notably sodium, potassium and lithium, preferably lithium.

"Alkaline-earth metal" means notably magnesium and calcium, preferably magnesium.

Preferably, M will represent lithium or magnesium linked to a halogen, preferably linked to chlorine or bromine.

"Protected form of $R^{2a}$" means notably the group —C≡C—SiR$^a$R$^b$R$^c$ when $R^{2a}$ represents the —C≡CH group, with R$^a$, R$^b$ and R$^c$ representing, independently of each other, a (C$_1$-C$_6$)alkyl group as defined above. Advantageously, SiR$^a$R$^b$R$^c$ represents a trimethylsilyl (TMS), tert-butyl-dimethylsilyl (TBDMS) or triisopropylsilyl (TIPS) group, preferably a TMS group. This protected form could then be deprotected in acid medium or in the presence of fluoride ions in order to release the —C≡CH function. Preferably, the —C≡C-TMS group will be deprotected in the presence of tert-butyl ammonium fluoride (TBAF).

According to a particular embodiment of the invention, the compound of formula (II) described above can be obtained by oxidation of the alcohol function of a compound of formula (IV) as follows:

HetAr—X—CH$_2$(OH)  (IV)

wherein HetAr and X are as previously defined.

Advantageously, this oxidation will be carried out by a Swern reaction, notably in the presence of dimethyl sulfoxide (DMSO) and trifluoroacetic anhydride (TFAA) or oxalyl chloride (ClCOOCCl), preferably in the presence of DMSO and ClCOOCCl. This reaction advantageously will be carried out in dichloromethane and advantageously at low temperature, notably at a temperature below −40° C., advantageously at approximately −50° C.

The present invention also relates to a method for preparing a compound of formula (I) as defined above wherein X represents an X1 chain as previously defined, wherein it comprises the following steps:
  Sonogashira coupling between a compound of formula (V) as follows:

  HetAr-Hal  (V), wherein Hal represents a chlorine or bromine atom and HetAr is as defined previously,
  and a compound of formula (VI) as follows:

  $R^2R^1CH\text{—}X1\text{-}H$  (VI), wherein $R^1$, $R^2$ and X1 are as previously defined,
  optionally hydrogenation of the triple bond of the compound obtained in the preceding step of Sonogashira coupling, and
  recovery of the compound of formula (I) obtained in the preceding step.

This method could be optionally followed by steps of functionalisation of the molecule well known to the person skilled in the art, notably at the terminal end of the aliphatic chain.

The Sonogashira coupling is carried out in the presence of a palladium catalyst, a copper(I) salt and a base.

The palladium catalyst could be advantageously $Pd(PPh_3)_2Cl_2$ or $Pd(PPh_3)_4$, preferably $Pd(PPh_3)_2Cl_2$.

The copper(I) salt can be CuI or CuBr, preferably CuI. The base can be an amine of formula $NR^dR^eR^f$, where $R^d$, $R^e$ and $R^f$ represent, independently of each other, a hydrogen atom or a $(C_1\text{-}C_6)$alkyl group as defined above. Preferably, this base is not ammonia ($NH_3$). Advantageously, it can be diethylamine ($NHEt_2$), triethylamine ($NEt_3$) or diisopropylethylamine ($(iPr)_2NEt$), preferably triethylamine.

This reaction will advantageously be carried out in tetrahydrofuran (THF) as solvent, and advantageously in THF at reflux.

"Hydrogenation" means, in the context of the present invention, partial or total hydrogenation, i.e. that the triple bond is hydrogenated in such as way as to yield a double bond or a single bond, respectively.

When X1 represents a saturated chain, it will thus be advisable to completely reduce the triple bond of the compound obtained during the Sonogashira coupling.

This triple bond could be reduced by hydrogenation under hydrogen atmosphere in the presence of a catalyst such as palladium on carbon. Advantageously, this reaction will be carried out in ethanol.

In addition, when X1 represents an unsaturated hydrocarbon chain comprising at least one double bond directly linked to HetAr, it will be advisable to partially reduce the triple bond to yield a double bond by carrying out partial hydrogenation. This reaction is well known to the person skilled in the art and can be carried out notably using a Lindlar catalyst.

According to an advantageous embodiment of this method, HetAr represents

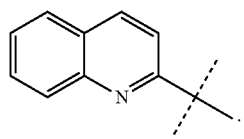

Equally advantageously, $R^2$ represents a hydrogen atom and $R^1$ is as defined previously, and advantageously represents a hydrogen atom or an OH group, preferably an OH group.

The present invention also relates to a method for preparing a compound of formula (I) as defined previously wherein X represents an —NH—CO—X2- group as defined previously, wherein it comprises the following steps:
  peptide coupling of a compound of formula (VII) as follows:

  $HetAr\text{—}NH_2$  (VII), wherein HetAr is as defined previously,
  with a compound of formula (VIII) as follows:

  $Z\text{—}X2\text{-}CHR^1R^2$  (VIII), wherein Z represents a carboxylic acid function optionally in activated form, and X2 is as defined previously,
  to yield the compound of formula (Ic) as follows:

  $HetAr\text{—}NHCO\text{—}X2\text{-}CHR^1R^2$  (Ic), wherein HetAr, $R^1$, $R^2$ and X2 are as previously defined, and
  recovery of compound (I) corresponding to compound (Ic) obtained in the preceding step.

This method could be optionally followed by steps of functionalisation of the molecule well known to the person skilled in the art, notably at the terminal end of the aliphatic chain.

"Activated form of carboxylic acid" means notably, in the context of the present invention, an acid chloride, i.e. a —COCl function in place of the carboxylic acid function —COOH.

Peptide coupling will be carried out advantageously in dichloromethane, preferably at room temperature (i.e. at a temperature between 15° C. and 40° C., preferably between 20° C. and 30° C., advantageously at approximately 25° C.).

When peptide coupling is carried out with an acid chloride, it could be envisaged to add a base to the reaction medium to encourage the reaction, such as an amine as previously defined. However, the reaction will be carried out preferably without an additional base in this case.

When peptide coupling is carried out with carboxylic acid, it will be carried out preferably in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU), optionally combined with a coupling auxiliary such as N-hydroxysuccinimide (NHS), N-hydroxybenzotriazole (HOBt), 3,4-dihydro-3-hydroxy-4-oxo-1,2,3-benzotriazole (HOOBt), 1-hydroxy-7-azabenzotriazole (HAt) or N-hydroxysulfosuccinimide (sulfo NHS). Preferably the pair EDC/HOBt will be used.

The present invention also relates to a method for preparing a compound of formula (I) as defined previously wherein X represents an —NH—CH₂—X3- group where X3 represents a linear, saturated or unsaturated hydrocarbon chain comprising from 7 to 19 carbon atoms, preferably from 9 to 15 carbon atoms, wherein it comprises the following steps:
  peptide coupling of a compound of formula (VII) as follows:

  $HetAr\text{—}NH_2$  (VII), wherein HetAr is as defined previously, with a compound of formula (IX) as follows:

Z—X3-CHR$^1$R$^2$     (IX), wherein Z represents a carboxylic acid function optionally in activated form, and X3 is as defined above, to yield the compound of formula (X) as follows:

HetAr—NHCO—X3-CHR$^1$R$^2$     (X), wherein HetAr, R$^1$ and R$^2$ are as previously defined and X3 is as defined above, reduction of the amide function to amine to yield the compound of formula (Id) as follows:

HetAr—NH—CH$_2$—X3-CHR$^1$R$^2$     (Id), wherein HetAr, R$^1$ and R$^2$ are as previously defined and X3 is as defined above, and recovery of compound (I) corresponding to compound (Id) obtained in the preceding step.

This method could be optionally followed by steps of functionalisation of the molecule well known to the person skilled in the art, notably at the terminal end of the aliphatic chain.

Peptide coupling will advantageously be carried out as defined above, for the preceding method.

Reduction of amide to amine will advantageously be carried out in the presence of a reducer such as LiAlH$_4$, advantageously in THF and preferably in THF at reflux.

Advantageously for the two preceding methods, R$^2$ represents a hydrogen atom and R$^1$ is as defined previously, and advantageously represents a hydrogen atom or an OH group, preferably a hydrogen atom.

According to an advantageous embodiment of the two preceding methods, HetAr represents

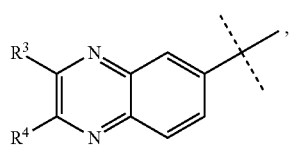

with R$^3$ and R$^4$ as defined above.

In this particular case,

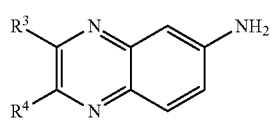

will be used as the starting product. Such a compound can be synthesized according to the following reaction pathway:

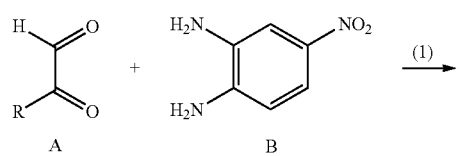

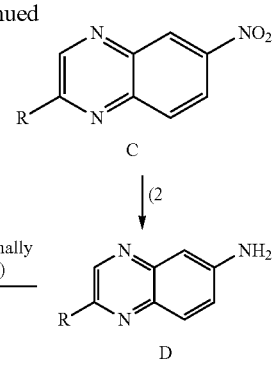

E     D (R = H or (C$_1$-C$_6$)alkyl)

In a first step (1), a ketoaldehyde A is condensed with 4-nitro-phenylene-1,2-diamine B to yield the nitro compound C which is then reduced in a second step to amine to yield the desired compound.

Step (1) is advantageously carried out at reflux of water.

The reducer used in step (2) is advantageously SnCl$_2$. This step is furthermore advantageously carried out in ethanol, preferably absolute ethanol, and advantageously at reflux of same.

Optional step (3) comprises the adding of R$^3$Li and then R$^4$Li to compound D, advantageously in THF and at low temperature, notably at approximately −78° C., followed by rearomatisation of the system by oxidation, notably in the presence of MnO$_2$, advantageously in chloroform, preferably at reflux of chloroform.

Depending on the R$^3$ and R$^4$ groups desired, this last step (3) may not be carried out or only R$^3$Li will be added but not R$^4$Li.

In addition, step (1) was carried out only with R representing a hydrogen atom or a methyl but other alkyl groups could be envisaged for this reaction.

The present invention will be better understood in the light of the non-restrictive figures and examples which follow.

BRIEF DESCRIPTION OF THE DRAWINGS

FIG. 4 represents the reuptake of tritiated dopamine per well, expressed as a percentage of the value of the untreated control, for the control, db-cAMP (200 μM) and for N3 (1 nM, 10 nM, 100 nM and 1 μM).

FIG. 5 represents the percentage of MAP2+ neurons in the wells, compared to the control value for N3 (10 nM and 100 nM).

FIG. 6 represents the reuptake of tritiated GABA per well, expressed as a percentage of the value of the untreated control, for the control and for N3 (10 nM and 100 nM).

EXAMPLES

Figure 1A:
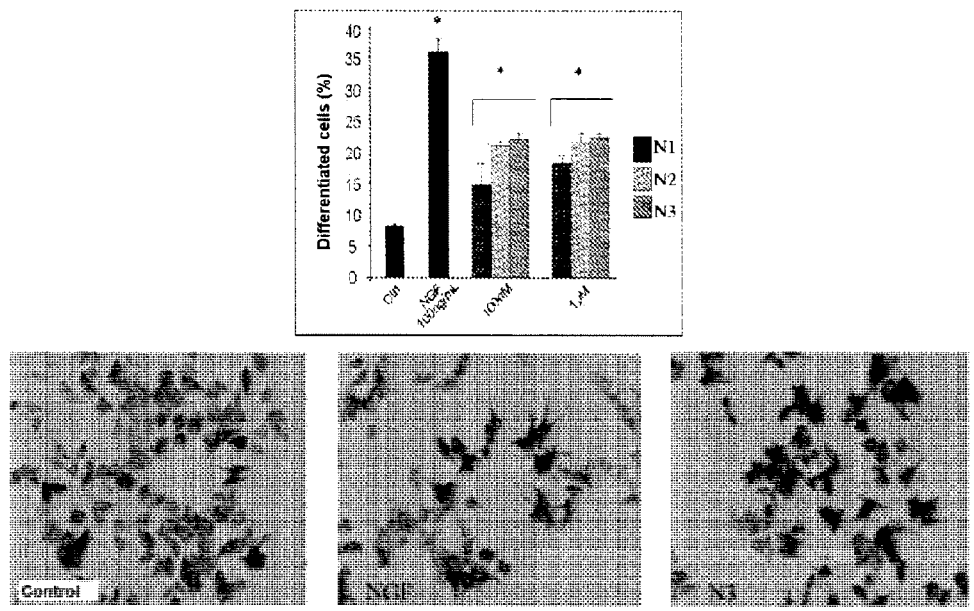
FIG. 1A represents the percentage of PC12 cells differentiated for the control, NGF (100 ng/ml) and for N1, N2 and N3 (100 nM and 1 μM). The graph is accompanied by three photographs representing the control cells and the cells obtained after treatment with NGF or N3 (100 nM), respectively.

Abbreviations used in the experimental section:
$^1$H NMR Proton nuclear magnetic resonance
$^{13}$C NMR Carbon nuclear magnetic resonance
IR Infrared absorption
ESI-MS Electrospray mass spectrometry
MS (EI) Electron impact mass spectrometry
eq Equivalent Example 1

Synthesis of the Molecules of the Invention

1. Synthesis of Quinoxaline Derivatives

These molecules were synthesized according to the following reaction scheme, with steps (3) and (5) being optional:

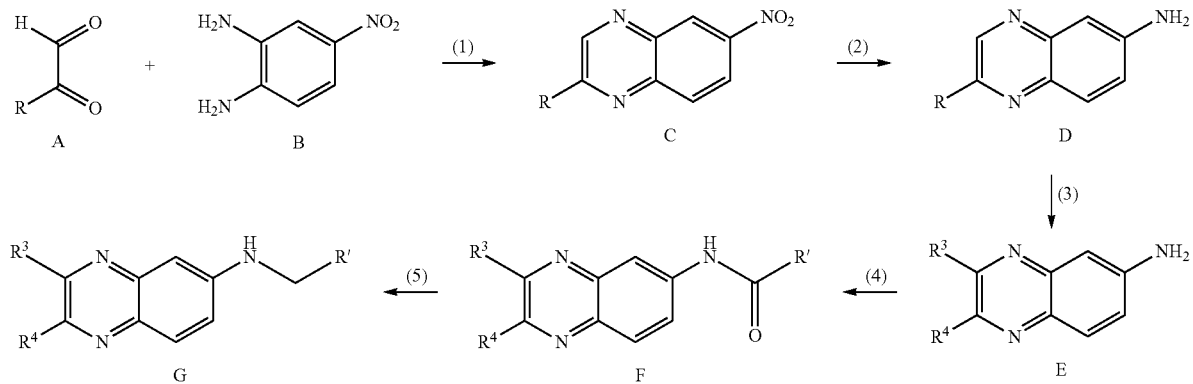

1.1. Step (1): Synthesis of Compounds C 1.1.1. Compound C1: 2-methyl-6-nitroquinoxaline

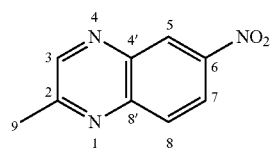

A mixture of 4-nitro-phenylene-1,2-diamine (3.06 g, 20 mmol) and pyruvic aldehyde (3.6 ml, 20 mmol, 40%) in water (50 ml) is heated at reflux for 1.5 h. After cooling, the reaction mixture is filtered under vacuum, washed with water and dissolved in dichloromethane. The solution is dried on anhydrous MgSO$_4$ and concentrated under vacuum.

Yield: 90%

$^1$H NMR (400 MHz, CDCl$_3$) δ ppm: 2.82 (s, 3H); 8.10 (d, J=8.4 Hz, 1H); 8.45 (d, J=8.0 Hz, 1H); 8.87 (s, 1H); 8.92 (s, 1H).

$^{13}$C NMR (50 MHz, CDCl$_3$) δ ppm: 22.8, 123.3, 125.5, 130.2, 139.7, 144.5, 147.0, 148.1, 157.3.

ESI-MS m/z: 190 ([M+H]$^+$, 100).

IR cm$^{-1}$: 715, 745, 795, 830, 860, 930, 940, 965, 1080, 1185, 1210, 1295, 1340, 1390, 1455, 1490, 1520, 1565, 1615, 2955, 3045.

1.1.2. Compound C2: 6-nitroquinoxaline

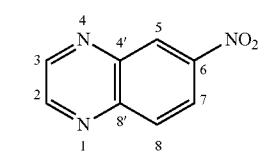

Glyoxal (2.8 ml, 24 mmol, 40%) is added slowly to a solution of 4-nitro-phenylene-1,2-diamine (1.53 g, 10 mmol) in water (30 ml). The mixture is heated at reflux for 4 h. After cooling, the reaction mixture is filtered under vacuum, washed with water and dissolved in dichloromethane. The solution is dried on anhydrous MgSO$_4$ and concentrated under vacuum.

Yield: 93%

$^1$H NMR (400 MHz, CDCl$_3$) δ ppm: 8.26 (d, J=9.2 Hz, 1H); 8.52 (dd, J=9.2 Hz, J=2.4 Hz, 1H); 9.01 (s, 3H).

$^{13}$C NMR (50 MHz, CDCl$_3$) δ ppm: 123.4, 125.9, 131.3, 141.9, 145.3, 147.0, 147.6, 147.9.

ESI-MS m/z: 176 ([M+H]$^+$, 23).

IR cm$^{-1}$: 740, 810, 850, 870, 930, 955, 1020, 1075, 1130, 1190, 1205, 1295, 1345, 1370, 14209, 1445, 1490, 1520, 1545, 1585, 1610, 3055, 3090.

1.2. Step (2): Synthesis of Compounds D

General Procedure:

To a solution of compound C (20 mmol) in absolute ethanol (50 ml) is added SnCl$_2$ (1.89 g, 100 mmol). The mixture is heated at reflux for 4 h under inert atmosphere of nitrogen. After cooling, the reaction mixture is basified to pH 8 with a saturated solution of NaHCO$_3$. The solution is filtered on celite and then washed with ethyl acetate. The recovered aqueous phase is extracted three times with ethyl acetate. The combined organic phases are washed with water saturated with NaCl, dried on anhydrous MgSO$_4$ and concentrated under vacuum.

1.2.1. Compound D1: 3-methyl-6-aminoquinoxaline

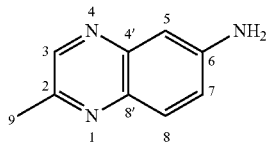

Yield: 80%

$^1$H NMR (300 MHz, CDCl$_3$) δ ppm: 2.62 (s, 3H); 4.22 (s, 2H); 7.09-7.11 (m, 2H); 7.73 (d, J=4.2 Hz, 1H); 8.52 (s, 1H).

$^{13}$C NMR (75 MHz, CDCl$_3$) δppm: 149.3, 147.1, 145.7, 142.5, 141.7, 136.8, 129.4, 121.7, 108.1, 121.8.

ESI-MS m/z: 160 ([M+H]$^+$, 100).

IR cm$^{-1}$: 3330, 3205, 3055, 2920, 1615, 1555, 1500, 1475, 1420, 1365, 1345, 1310, 1230, 1210, 1170, 1130, 1015, 970, 940, 910, 830, 780, 755, 730.

1.2.2. Compound D2: 6-aminoquinoxaline

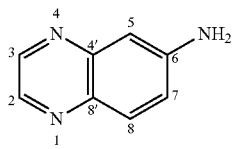

Yield: 80%

$^1$H NMR (400 MHz, CDCl$_3$) δ ppm: 4.10 (s, 2H); 7.12 (d, J=2.4 Hz, 1H); 7.15 (dd, J=8.8 Hz, J=2.4 Hz, 1H); 7.84 (d, J=8.8 Hz, 1H); 8.52 (s, 1H); 8.62 (s, 1H).

$^{13}$C NMR (50 MHz, CDCl$_3$) δ ppm: 148.1, 144.9, 140.9, 137.9, 130.3, 122.0, 107.8.

ESI-MS m/z: 146 ([M+H]$^+$, 100).

IR cm$^{-1}$: 3395, 3315, 3185, 3055, 1645, 1615, 1545, 1500, 1470, 1435, 1370, 1310, 1225, 1210, 1135, 1030, 960, 860, 815, 765.

1.3. Step (3): Synthesis of Compounds E

1.3.1. Synthesis by Adding R$^3$Li only (thus R$^4$=H or Me)

General Procedure:

The organolithium R$^3$Li (2.5 mmol) is added slowly to a solution of compound D (1 mmol) in anhydrous THF at −78° C. under inert atmosphere of nitrogen. The solution becomes reddish-black. The reaction mixture is stirred at −78° C. for 2.5 h and then hydrolyzed by a saturated aqueous NH$_4$Cl solution, extracted with ethyl acetate and then washed with water saturated with NaCl. The organic phase is then dried on anhydrous MgSO$_4$ and concentrated under reduced pressure. The residue obtained is dissolved in CHCl$_3$ (20 ml) and then MnO$_2$ (5 mmol, 430 mg) is added and the solution is heated at reflux for 4 h. The reaction is hydrolyzed by 2 ml water, filtered on celite and washed with ethyl acetate. The organic phase is dried on anhydrous MgSO$_4$ and concentrated under reduced pressure. The products are purified on a silica column in a mixture of cyclohexane and ethyl acetate in a proportion of 2:8.

1.3.1.1. Compound E1: 2-methyl-3-butyl-6-aminoquinoxaline

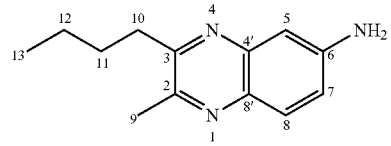

Yield: 75%

$^1$H NMR (300 MHz, CDCl$_3$) δ ppm: 0.98 (t, J=7.2 Hz, 3H); 1.47 (m, 2H); 1.77 (m, 2H); 2.90 (t, J=7.8 Hz, 2H); 4.04 (s, 2H); 7.07 (m, 2H); 7.75 (d, J=8.1 Hz, 1H).

$^{13}$C NMR (75 MHz, CDCl$_3$) δ ppm: 13.9, 22.3, 22.8, 30.5, 35.7, 108.1, 120.5, 129.1, 135.7, 142.7, 146.9, 148.9, 156.9.

ESI-MS m/z: 216 ([M+H]$^+$, 100).

IR cm$^{-1}$: 705, 740, 780, 790, 830, 855, 875, 955, 970, 1010, 1075, 1105, 1130, 1160, 1250, 1285, 1315, 1345, 1375, 1460, 1500, 1555, 1620, 1655, 2870, 2925, 2955, 3170, 3320.

1.3.1.2. Compound E2: 2-methyl-3-hexyl-6-aminoquinoxaline

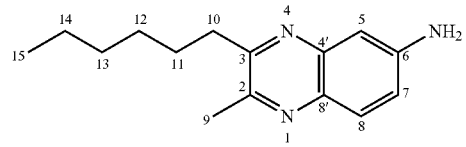

Yield: 65%

$^1$H NMR (300 MHz, CDCl$_3$) δ ppm: 0.89 (t, J=6.6 Hz, 3H); 1.25-1.60 (m, 8H); 2.68 (s, 3H); 2.92 (t, J=8.1 Hz, 2H); 4.05 (s, 2H); 7.06 (m, 2H); 7.77 (d, J=8.4 Hz, 1H).

$^{13}$C NMR (75 MHz, CDCl$_3$) δ ppm: 14.0, 22.3, 22.6, 28.4, 29.4, 31.6, 108.2, 120.5, 129.16, 135.7, 142.8, 146.9, 148.8, 156.9.

ESI-MS m/z: 244 ([M+H]$^+$, 100).

IR cm$^{-1}$: 830, 1005, 1080, 1135, 1240, 1345, 1375, 1465, 1500, 1545, 1585, 1620, 1690, 2005, 2145, 2345, 2360, 2855, 2925, 2955, 3225, 3340

1.3.1.3. Compound E3: 2-methyl-3-secbutyl-6-aminoquinoxaline

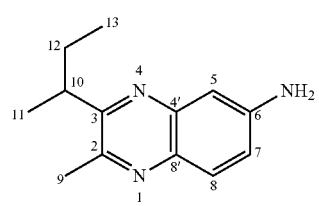

Yield: 65%

¹H NMR (300 MHz, CDCl₃) δ ppm: 0.89 (t, J=7.5 Hz, 3H); 1.32 (d, J=6.9 Hz, 3H); 1.63 (m, 1H); 1.92 (m, 1H); 2.69 (s, 3H); 3.14 (q, J=6.9 Hz, 1H); 4.02 (s, 2H); 7.09 (m, 2H); 7.74 (d, J=8.7 Hz, 1H).

¹³C NMR (75 MHz, CDCl₃) δ ppm: 12.3, 19.3, 22.4, 28.9, 38.9, 108.5, 120.5, 129.0, 135.3, 140.6, 146.8, 148.7, 160.7.

ESI-MS m/z: 216 ([M+H]⁺, 100).

IR cm⁻¹: 730, 830, 855, 910, 1000, 1020, 1050, 1075, 1130, 1180, 1235, 1320, 1375, 1460, 1500, 1555, 1620, 2360, 2870, 2925, 2960, 3220, 3345.

1.3.1.4. Compound E4: 2-methyl-3-tertbutyl-6-aminoquinoxaline

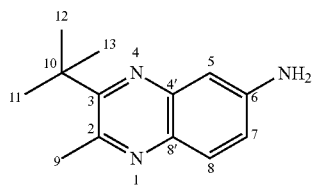

Yield: 25%

¹H NMR (300 MHz, CDCl₃) δ ppm: 1.51 (s, 9H); 2.84 (s, 3H); 4.22 (s, 2H); 7.09 (m, 2H); 7.73 (d, J=9.0 Hz, 1H).

¹³C NMR (75 MHz, CDCl₃) δ ppm: 25.7, 29.4, 108.8, 120.7, 128.7, 134.9, 141.5, 146.8, 148.4, 162.2.

ESI-MS m/z: 216 ([M+H]⁺, 100).

IR cm⁻¹: 730, 785, 830, 855, 910, 1000, 1070, 1130, 1200, 1245, 1325, 1365, 1395, 1410, 1455, 1495, 1545, 1565, 1620, 2360, 2870, 2930, 2965, 3220, 3340.

1.3.1.5. Compound E5: 2-methyl-3-phenyl-6-aminoquinoxaline

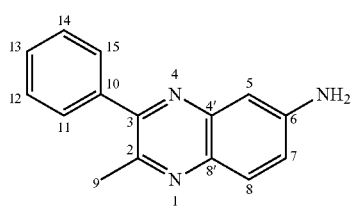

Yield: 75%

¹H NMR (300 MHz, CDCl₃) δ ppm: 2.68 (s, 3H); 3.88 (s, 2H); 7.16 (m, 2H); 7.48 (m, 3H); 7.61 (m, 2H); 7.83 (d, J=8.7 Hz, 1H).

¹³C NMR (75 MHz, CDCl₃) δ ppm: 23.8, 108.4, 121.7, 128.4, 128.7, 128.9, 129.2, 136.2, 139.4, 142.6, 147.3, 148.0, 154.8.

ESI-MS m/z: 236 ([M+H]⁺, 100).

IR cm⁻¹: 725, 775, 830, 905, 970, 1005, 1160, 1255, 1325, 1345, 1380, 1420, 1490, 1515, 1560, 1625, 1965, 2215, 2480, 2925, 2965, 3210.

1.3.1.6. Compound E6: 3-butyl-6-aminoquinoxaline

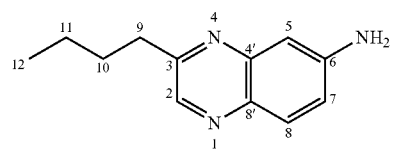

Yield: 54%

¹H NMR (400 MHz, CDCl₃) δ ppm: 0.93 (t, J=7.2 Hz, 3H); 1.38-1.48 (m, 2H); 1.74-1.82 (m, 2H); 2.89 (t, J=7.5 Hz, 2H); 4.17 (s, 2H); 7.08-7.11 (m, 2H); 7.81 (d, J=8.1 Hz, 1H); 8.44 (s, 1H).

¹³C NMR (50 MHz, CDCl₃) δ ppm: 13.9, 22.6, 31.7, 36.2, 107.9, 120.7, 130.1, 136.1, 141.8, 144.0, 147.9, 157.7.

ESI-MS m/z: 202 ([M+H]⁺, 100).

IR cm⁻¹: 730, 775, 830, 855, 905, 955, 995, 1080, 1130, 1165, 1240, 1275, 1370, 1435, 1465, 1510, 1550, 1620, 2860, 2930, 2955, 3210, 3335.

1.3.1.7. Compound E7: 3-hexyl-6-aminoquinoxaline

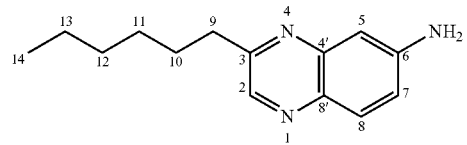

Yield: 53

¹H NMR (400 MHz, CDCl₃) δ ppm: 0.87 (t, J=6.9 Hz, 3H); 1.22-1.35 (m, 6H); 1.77 (m, 4H); 2.88 (t, J=7.8 Hz, 2H); 4.14 (s, 2H); 7.09 (m, 2H); 7.80 (d, J=8.7 Hz, 1H); 8.42 (s, 1H).

¹³C NMR (50 MHz, CDCl₃) δ ppm: 14.0, 22.5, 29.1, 29.6, 31.6, 36.5, 108.0, 120.7, 130.0, 136.1, 141.8, 144.0, 147.9, 157.7.

ESI-MS m/z: 230 ([M+H]⁺, 100).

IR cm⁻¹: 730, 775, 830, 905, 975, 1080, 1135, 1160, 1185, 1235, 1280, 1340, 1370, 1465, 1510, 1550, 1620, 2360, 2855, 2925, 2955, 3215, 3340.

1.3.1.8. Compound E8: 3-secbutyl-6-aminoquinoxaline

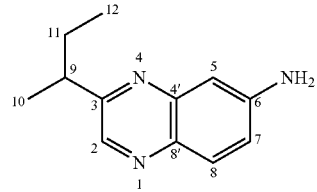

Yield: 40%

¹H NMR (300 MHz, CDCl₃) δ ppm: 0.90 (t, J=7.5 Hz, 3H); 1.37 (d, J=7.2 Hz, 3H); 1.73 (m, 1H); 1.88 (m, 1H); 2.96 (m, 1H); 4.12 (s, 2H); 7.09 (m, 2H); 7.84 (d, J=9.6 Hz, 1H); 8.45 (s, 1H).

¹³C NMR (75 MHz, CDCl₃) δ ppm: 12.1, 19.9, 29.6, 42.1, 108.1, 120.7, 130.0, 136.3, 141.0, 144.0, 147.8, 161.4.

ESI-MS m/z: 202 ([M+H]⁺, 100).

IR cm⁻¹: 735, 775, 830, 855, 905, 960, 980, 1015, 1050, 1085, 1130, 1175, 1230, 1250, 1275, 1370, 1430, 1460, 1510, 1545, 1620, 2360, 2875, 2925, 2960, 3215, 3340.

1.3.1.9. Compound E9: 3-tertbutyl-6-aminoquinoxaline

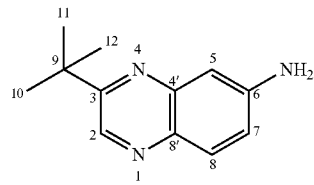

Yield: 26%

¹H NMR (300 MHz, CDCl₃) δ ppm: 1.44 (s, 9H); 4.21 (s, 2H); 7.05 (m, 1H); 7.78 (d, J=9.3 Hz, 1H); 8.67 (s, 1H).

¹³C NMR (75 MHz, CDCl₃) δ ppm: 29.6, 36.9, 108.2, 120.7, 127.9, 135.6, 139.1, 143.2, 147.8, 163.6.

ESI-MS m/z: 202 ([M+H]⁺, 100).

IR cm⁻¹: 730, 775, 830, 855, 905, 955, 975, 1020, 1110, 1200, 1245, 1280, 1365, 1430, 1460, 1505, 1545, 1620, 2960, 3215, 3335.

1.3.1.10. Compound E10: 3-phenyl-6-aminoquinoxaline

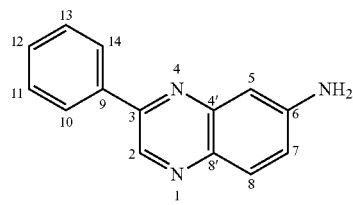

Yield: 28%

¹H NMR (300 MHz, CDCl₃) δ ppm: 4.12 (s, 2H); 7.08 (m, 2H); 7.45 (m, 3H); 7.82 (d, J=9.6 Hz, 1H); 8.08 (d, J=9.5 Hz, 2H); 8.95 (s, 1H).

1.3.2. Synthesis by adding R³Li and then R⁴Li

General Procedure:

The first organolithium R³Li (2.5 mmol) is added slowly to a solution of compound D (1 mmol) in anhydrous THF at −78° C. under inert atmosphere of nitrogen. The solution becomes reddish-black. The mixture is stirred at −78° C. for 2.5 h. The mixture is placed at 0° C. and the second organolithium R⁴Li (2 mmol) is immediately added slowly. The mixture is stirred at 0° C. for 2 h. The reaction is hydrolyzed by a saturated aqueous NH₄Cl solution and extracted with ethyl acetate. The organic phase is washed with water saturated with NaCl, dried on anhydrous MgSO₄ and concentrated under reduced pressure. The residue obtained is dissolved in CHCl₃ (20 ml) and then MnO₂ (5 mmol, 430 mg) is added and the mixture carried at reflux for 4 h. The reaction is hydrolyzed and then filtered on celite. The organic phase is dried on anhydrous MgSO₄ and concentrated under vacuum. The products are purified on a silica column in a mixture of cyclohexane and ethyl acetate in a proportion of 5:5.

1.3.2.1. Compound E11: 2-butyl-3-hexyl-6-aminoquinoxaline

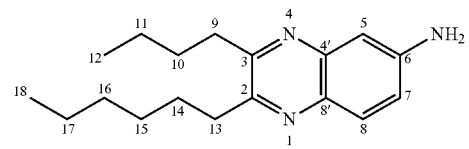

Yield: 30%

¹H NMR (300 MHz, CDCl₃) δ ppm: 0.96 (m, 6H); 1.31-1.32 (m, 8H); 1.40-1.52 (m, 2H); 1.68-1.79 (m, 2H); 2.9 (m, 4H); 4.10 (s, 2H); 7.05 (m, 2H); 7.74 (d, J=9.6 Hz, 1H).

¹³C NMR (75 MHz, CDCl₃) δ ppm: 13.9, 14.0, 22.5, 29.1, 29.2, 29.3, 29.4, 31.6, 35.1, 35.4, 108.0, 120.5, 129.3, 135.8, 142.5, 146.9, 152.6, 156.6.

ESI-MS m/z: 286 ([M+H]⁺, 40).

IR cm⁻¹: 725, 830, 855, 930, 960, 1080, 1135, 1235, 1340, 1465, 1500, 1620, 2925, 2855, 2955, 3215, 3335.

1.3.2.2. Compound E12: 2-hexyl-3-butyl-6-aminoquinoxaline

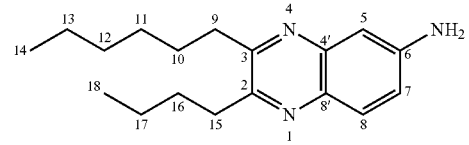

Yield: 35%

¹H NMR (300 MHz, CDCl₃) δ ppm: 0.92 (m, 6H); 1.25-1.45 (m, 8H); 1.72-1.82 (m, 4H); 2.92 (m, 4H); 4.06 (s, 2H); 7.06 (m, 2H); 7.77 (d, J=7.8 Hz, 1H).

¹³C NMR (75 MHz, CDCl₃) δ ppm: 13.9, 14.0, 22.5, 22.8, 29.0, 29.1, 29.4, 31.6, 35.1, 35.4, 108.0, 120.5, 129.2, 135.8, 142.5, 146.9, 152.5, 156.6.

ESI-MS m/z: 286 ([M+H]⁺, 100).

IR cm⁻¹: 730, 830, 855, 905, 960, 1075, 1135, 1170, 1235, 1345, 1465, 1500, 1550, 1625, 2860, 2930, 2955, 3215, 3335.

1.3.2.3. Compound E13: 2-butyl-3-phenyl-6-aminoquinoxaline

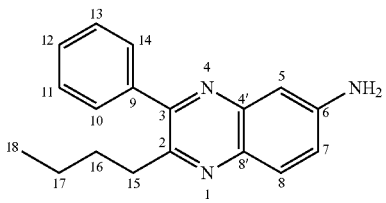

Yield: 30%

$^1$H NMR (300 MHz, CDCl$_3$) δ ppm: 0.82 (t, J=7.2 Hz, 3H); 1.25 (m, 4H); 1.67 (t, J=7.8 Hz, 2H); 2.95 (t, J=7.8 Hz, 2H); 4.15 (s, 2H); 7.13 (m, 2H); 7.43-7.58 (m, 5H); 7.88 (d, J=8.7 Hz, 1H).

$^{13}$C NMR (75 MHz, CDCl$_3$) δ ppm: 13.7, 22.6, 26.8, 31.3, 35.6, 107.5, 121.1, 128.0, 128.2, 128.3, 128.8, 129.6, 129.7, 130.1, 135.6, 139.5, 143.2, 147.7, 151.1, 156.2.

ESI-MS m/z: 278 ([M+H]$^+$, 100).

IR cm$^{-1}$: 730, 765, 830, 855, 910, 965, 1010, 1075, 1135, 1240, 1345, 1420, 1445, 1460, 1495, 1560, 1580, 1620, 2855, 2925, 2955, 3060, 3215, 3335.

1.4. Step (4): Synthesis of compounds F

1.4.1. Peptide Coupling in the Presence of Acid Chloride

General Procedure:

To a solution of acid R'COOH (484 mg, 2 mmol) in dichloromethane (10 ml) placed at 0° C. under inert atmosphere of nitrogen are added three drops of dry dimethylformamide (DMF) and oxalyl chloride (1.04 ml, 12 mmol). The mixture is stirred at 0° C. for 1 h. The dichloromethane and the excess oxalyl chloride are evaporated at 70° C. under reduced pressure. The acid chloride R'COCl thus obtained is dissolved in 5 ml dichloromethane.

To a solution of compound D or E (1 mmol) in dichloromethane (10 ml) at 0° C. under atmosphere of nitrogen are added triethylamine (0.55 ml, 2 mmol) and slowly the acid chloride in solution in dichloromethane (5 ml). The reaction mixture is stirred at room temperature for 2 h. The reaction is hydrolyzed with water and then extracted with dichloromethane. The organic phase is dried on anhydrous MgSO$_4$ and then concentrated under vacuum. The products are purified on a silica column in a mixture of cyclohexane and ethyl acetate in a proportion of 8:2.

1.4.1.1. Compound F1: Nr-(quinoxalin-6-yl)pentadecanamide

Yield: 70%

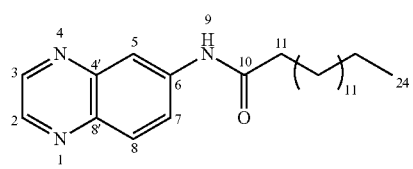

$^1$H NMR (300 MHz, CDCl$_3$) δ ppm: 0.88 (t, J=6.9 Hz, 3H); 1.25 (m, 18H); 1.68 (m, 6H); 2.45 (t, J=7.5 Hz, 2H); 7.58 (s, 1H); 8.04 (m, 2H); 8.27 (s, 1H); 8.74 (d, J=1.5 Hz, 1H); 8.79 (d, J=1.5 Hz, 1H).

$^{13}$C NMR (50 MHz, CDCl$_3$) δ ppm: 14.1, 22.7, 25.5, 29.4, 29.5, 29.6, 31.9, 37.9, 116.8, 124.0, 130.1, 139.5, 140.2, 143.7, 145.4, 171.9.

ESI-MS m/z: 370 ([M+H]$^+$, 100).

IR cm$^{-1}$: 732, 786, 832, 957, 1026, 1217, 1355, 1498, 1542, 1583, 1619, 1671, 1749, 2851, 2921, 3054, 3304.

1.4.1.2. Compound F2: N-(2-methylquinoxalin-6-yl)pentadecanamide

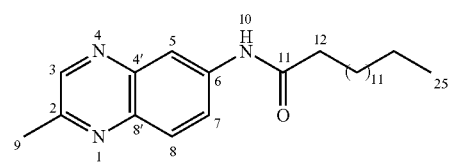

Yield: 68%

$^1$H NMR (300 MHz, CDCl$_3$) δ ppm: 0.88 (t, J=6.9 Hz, 3H); 1.25 (m, 20H); 1.68 (m, 4H); 2.44 (t, J=7.8 Hz, 2H); 2.75 (s, 1H); 7.40 (s, 1H); 7.95 (s, 2H); 8.20 (s, 1H); 8.70 (s, 1H).

$^{13}$C NMR (50 MHz, CDCl$_3$) δ ppm: 14.1, 22.4, 22.7, 25.6, 29.4, 29.5, 29.7, 31.9, 37.9, 117.0, 123.9, 138.4, 139.3, 141.5, 146.5, 152.6, 171.7.

IR cm$^{-1}$: 727, 836, 972, 1211, 1377, 1495, 1540, 1582, 1620, 1673, 2854, 2925, 3285.

1.4.1.3. Compound F3: N-(3-butylquinoxalin-6-yl)pentadecanamide

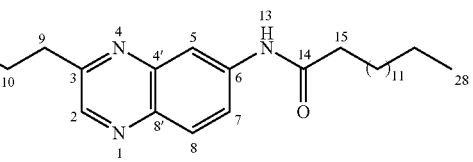

Yield: 75%

$^1$H NMR (200 MHz, CDCl$_3$) δ ppm: 0.87 (t, J=6.8 Hz, 3H); 0.96 (t, J=6.9 Hz, 3H); 1.25 (m, 20H); 1.76 (m, 4H); 2.43 (t, J=7.2 Hz, 2H); 2.98 (t, J=7.6 Hz, 2H); 7.65 (s, 1H); 7.89 (dd, J=2.2 Hz, J=9.0 Hz, 1H); 7.98 (d, J=9.0 Hz, 1H); 8.17 (d, J=2.2 Hz, 1H); 8.62 (s, 1H).

$^{13}$C NMR (50 MHz, CDCl$_3$) δ ppm: 13.9, 14.1, 22.5, 22.7, 25.6, 29.4, 29.5, 29.7, 31.5, 31.9, 36.2, 116.5, 122.7, 129.8, 132.5, 138.4, 142.8, 144.6, 158.2, 171.8.

IR cm$^{-1}$: 726, 838, 1000, 1236, 1373, 1502, 1537, 1583, 1620, 1671, 2853, 2923, 3298.

1.4.1.4. Compound F4: N-(2-hexyl-3-butylquinoxalin-6-yl)pentadecanamide

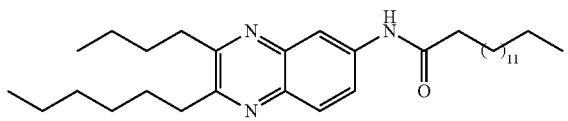

Yield: 92%

¹H NMR (300 MHz, CDCl₃) δ ppm: 0.83 (t, J=6.8 Hz, 6H); 0.87 (t, J=6.8 Hz, 3H); 0.96 (t, J=6.9 Hz, 3H); 1.25 (m, 20H); 1.50 (m, 4H); 1.71 (m, 6H); 1.76 (m, 8H); 2.43 (t, J=7.2 Hz, 2H); 2.98 (m, 4H); 7.36 (s, 1H); 7.86 (d, J=9.0 Hz, 1H); 7.93 (d, J=9.0 Hz, 1H); 8.11 (s, 1H).

¹³C NMR (50 MHz, CDCl₃) δ ppm: 14.0, 14.1, 22.7, 22.8, 24.8, 25.6, 26.9, 29.1, 29.4, 29.7, 30.2, 30.9, 31.7, 31.9, 34.0, 34.9, 116.5, 122.6, 128.9, 138.3, 141.2, 149.4, 150.7, 157.1, 178.9.

ESI-MS m/z: 510 ([M+H]⁺, 100).

IR cm⁻¹: 728, 837, 1039, 1241, 1378, 1496, 1539, 1579, 1620, 1709, 2853, 2923, 2956, 3300.

1.4.2. Peptide Coupling in the Presence of Carboxylic Acid

1.4.2.1. Compound F5: 24-hydroxy-N-(quinoxalin-6-yl)pentadecanamide

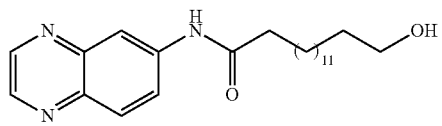

To a solution of 6-aminoquinoxaline (290 mg, 2 mmol) and hydroxypentadecanoic acid (518 mg, 2 mmol) in dichloromethane (40 ml) are added triethylamine (0.83 ml, 6 mmol), EDC (768 mg, 4 mmol) and HOBt (405 mg, 3 mmol). The mixture is stirred overnight at room temperature under inert atmosphere of nitrogen. The reaction is hydrolyzed, extracted with dichloromethane and then washed with a concentrated NH₄Cl solution. The organic phase is dried on anhydrous MgSO₄ and concentrated under reduced pressure. The residue obtained is then dissolved in DMF (10 ml), and then imidazole (136 mg, 2 mmol) and TBDMS-Cl (332 mg, 2.2 mmol) are added. The mixture is stirred overnight at room temperature under inert atmosphere of nitrogen. The reaction is hydrolyzed and then extracted with ethyl acetate, dried on anhydrous MgSO₄ and concentrated under vacuum. The silylated product is purified on a silica column in a mixture of cyclohexane and ethyl acetate in a proportion of 8:2. The product is then dissolved in THF (10 ml) and TBAF (3 ml, 1M in THF) is added. After 5 minutes the reaction is hydrolyzed and extracted with ethyl acetate. The organic phase is dried on anhydrous MgSO₄ and concentrated under vacuum. The product is obtained with a total yield of 38% on three steps.

Yield: 38% (3 steps)

¹H NMR (400 MHz, CDCl₃) δ ppm: 1.30 (m, 24H); 1.75 (m, 4H); 2.42 (t, J=7.5 Hz, 2H); 3.61 (t, J=6.6 Hz, 2H); 7.60 (s, 1H); 8.06 (t, J=9 Hz, 2H); 8.24 (d, J=2.1 Hz, 1H); 8.77 (s, 1H); 8.81 (s, 1H).

¹³C NMR (100 MHz, CDCl₃) δ ppm: 13.0, 24.9, 25.6, 29.5, 33.9, 49.2, 101.0, 107.1, 111.5, 125.2, 155.7, 182.2.

IR cm⁻¹: 641, 720, 803, 832, 892, 959, 1029, 1069, 1087, 1185, 1227, 1243, 1271, 1310, 1347, 1436, 1449, 1463, 1503, 1572, 1624, 1678, 2849, 2916, 3323.

1.5. Step (5): Synthesis of Compounds G

General Procedure:

To a solution of amide F (1 mmol) in THF (10 ml) placed at 0° C. under inert atmosphere of nitrogen, LiAlH₄ (304 mg, 8 mmol) is added slowly in small portions. The mixture is then heated at reflux for 2 h. After cooling, the reaction is hydrolyzed gently with 1 ml water, and then a 1M NaOH solution is added drop by drop until a white precipitate is obtained. The mixture is filtered on celite, washed with ethyl acetate and then dried on anhydrous MgSO₄ and concentrated under vacuum.

1.5.1. Compound G1: N-(quinoxalin-6-yl)pentadecanamine

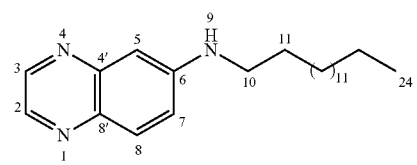

Yield: quantitative

¹H NMR (300 MHz, CDCl₃) δ ppm: 0.87 (t, J=6.9 Hz, 3H); 1.25 (m, 22H); 1.68 (m, 4H); 3.26 (t, J=6.9 Hz, 2H); 4.15 (s, 1H); 6.94 (s, 1H); 7.10 (dd, J=1.5 Hz, J=7.2 Hz, 1H); 7.72 (d, J=8.7 Hz, 1H); 8.49 (s, 1H); 8.63 (s, 1H).

¹³C NMR (50 MHz, CDCl₃) δ ppm: 14.1, 22.7, 27.2, 29.1, 29.4, 29.7, 31.9, 43.8, 103.3, 122.2, 130.0, 137.2, 140.1, 144.8, 145.5, 149.4.

ESI-MS m/z: 356 ([M+H]⁺, 100).

IR cm⁻¹: 556, 578, 594, 614, 650, 729, 818, 858, 905, 949, 1035, 1080, 1132, 1211, 1234, 1310, 1350, 1440, 1465, 1522, 1578, 1621, 1910, 2000, 2254, 2361, 2852, 2922, 3306.

1.5.2. Compound G2: N-(2-methylquinoxalin-6-yl)pentadecanamine

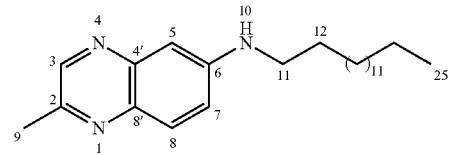

Yield: quantitative

¹H NMR (300 MHz, CDCl₃) δ ppm: 0.87 (t, J=6.9 Hz, 3H); 1.25 (m, 23H); 1.68 (m, 3H); 2.66 (s, 3H); 3.23 (t, J=6.9 Hz, 2H); 4.10 (s, 1H); 6.93 (d, J=2.4 Hz, 1H); 7.06 (dd, J=2.7 Hz, J=9 Hz, 1H); 7.72 (d, J=9 Hz, 1H); 8.54 (s, 1H).

¹³C NMR (50 MHz, CDCl₃) δ ppm: 14.1, 21.2, 22.7, 27.2, 29.2, 29.4, 29.7, 31.9, 43.8, 103.7, 121.9, 129.1, 136.9, 141.2, 143.3, 145.6, 148.6.

ESI-MS m/z: 370 ([M+H]⁺, 100).

IR cm$^{-1}$: 730, 823, 906, 970, 1082, 1232, 1354, 1376, 1466, 1519, 1622, 2852, 2922, 3296.

1.5.3. Compound G3:
N-(3-butylquinoxalin-6-yl)pentadecanamine

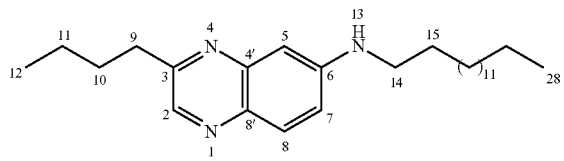

Yield: quantitative $^1$H NMR (300 MHz, CDCl$_3$) δ ppm: 0.88 (t, J=6.6 Hz, 3H); 0.96 (t, J=7.2 Hz, 3H); 1.25 (m, 30H); 1.79 (m, 4H); 2.91 (t, J=7.8 Hz, 2H); 3.24 (t, J=7.2 Hz, 2H); 4.15 (s, 1H); 6.90 (d, J=2.4 Hz, 1H); 7.01 (dd, J=2.7 Hz, J=9 Hz, 1H); 7.77 (d, J=9 Hz, 1H), 8.39 (s, 1H).

$^{13}$C NMR (50 MHz, CDCl$_3$) δ ppm: 13.9, 14.1, 22.7, 27.2, 29.1, 29.4, 29.7, 31.9, 43.8, 103.2, 120.9, 129.7, 136.0, 140.8, 144.7, 149.4, 157.5.

IR cm$^{-1}$: 729, 824, 905, 1081, 1245, 1375, 1521, 1623, 2853, 2924, 3308.

1.5.4. Compound G4:
N-(2-hexyl-3-butylquinoxalin-6-yl)pentadecanamine

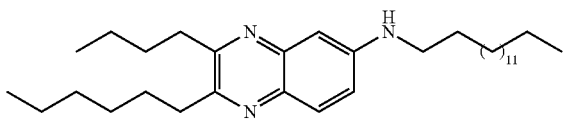

Yield: 85%

$^1$H NMR (300 MHz, CDCl$_3$) δ ppm: 0.88 (t, J=6.9 Hz, 3H); 0.98 (t, J=7.2 Hz, 3H); 1.25 (m, 36H); 1.77 (m, 8H); 2.91 (t, J=7.2 Hz, 2H); 2.94 (t, J=7.2 Hz, 2H); 3.23 (t, J=7.2 Hz, 2H); 4.03 (s, 1H); 6.91 (d, J=2.4 Hz, 1H); 6.98 (dd, J=2.7 Hz, J=9 Hz, 1H); 7.72 (d, J=9 Hz, 1H)

$^{13}$C NMR (50 MHz, CDCl$_3$) δ ppm: 14.0, 14.1, 22.6, 22.7, 23.0, 27.2, 29.2, 29.4, 29.5, 29.7, 31.5, 31.7, 31.9, 34.8, 35.1, 35.3, 43.9, 103.3, 120.6, 129.0, 135.7, 143.2, 148.6, 151.6, 156.3.

ESI-MS m/z: 496 ([M+H]$^+$, 100).

IR cm$^{-1}$: 730, 822, 906, 1078, 1239, 1356, 1513, 1568, 1622, 2854, 2924, 2956, 3294.

1.5.5. Compound G5:
15-hydroxy-N-(quinoxalin-6-yl)pentadecylamine

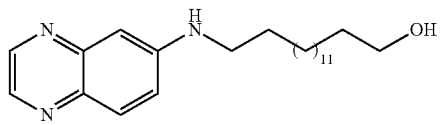

Yield: quantitative $^1$H NMR (400 MHz, CDCl$_3$) δ ppm: 1.25 (m, 26H); 1.52 (m, 4H); 3.18 (t, J=7.5 Hz, 2H); 3.53 (t, J=6.6 Hz, 2H); 5.23 (s, 1H); 6.35 (s, 1H); 7.02 (d, 1H); 7.65 (d, 1H), 8.03 (m, 1H); 8.41 (s, 1H); 8.53 (s, 1H).

$^{13}$C NMR (100 MHz, CDCl$_3$) δ ppm: 17.3, 25.6, 27.1, 29.6, 32.8, 33.1, 103.0, 141.0, 144.2, 147.3.

IR cm$^{-1}$: 573, 650, 726, 822, 859, 904, 1077, 1136, 1236, 1352, 1465, 1518, 1622, 1677, 2254, 2853, 2923, 3312.

2. Synthesis of Quinoline Derivatives

These molecules were synthesized according to the following reaction scheme, steps (3) and (5) being optional:

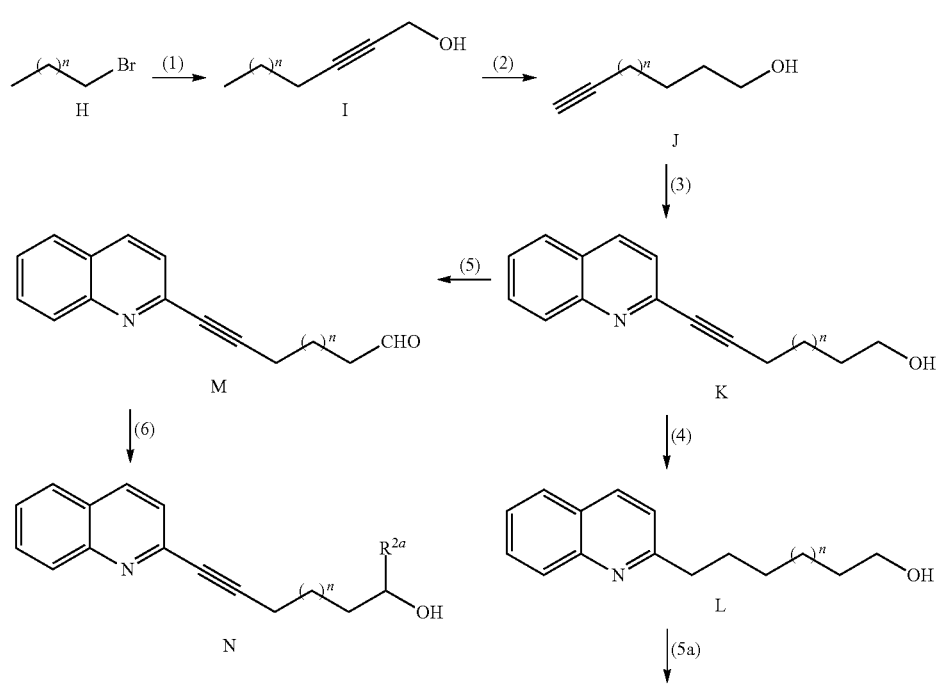

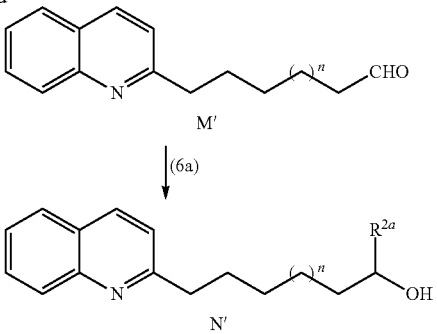

2.1. Step (1): Synthesis of alc-2-yn-1-ol I

General Procedure:

To an ammonia solution (100 ml) condensed at −35° C. under inert atmosphere of nitrogen, $10^{-3}$ mmol (0.05 eq) of lithium chips are added. A catalytic quantity of $Fe(NO_3)_3$ is then added followed by 0.150 mmol (3 eq) of lithium chips. A metal deposit appears and disappears in 15 minutes. Distilled propargyl alcohol (75 mmol, 1.5 eq) dissolved in THF (20 ml) is introduced drop by drop. After 15 minutes of stirring, bromoalkane H (50 mmol, 1 eq) dissolved in THF (20 ml) is added drop by drop. The solution is stirred for 6 h and then the ammonia is evaporated under a hood. After one night, the solution is hydrolyzed and extracted with dichloromethane. The organic phase is dried on $MgSO_4$, and then filtered and evaporated under vacuum. Purification is carried out by filtration on a silica gel in a mixture of cyclohexane and ethyl acetate in a proportion of 8:2.

2.1.1. Compound I1: undec-2-yn-1-ol

Yield: 58%

$^1$H NMR (200 MHz, $CDCl_3$) δ ppm: 0.88 (t, J=6.8 Hz, 3H); 1.27-1.54 (m, 10H); 2.21 (tt, J=2.3 Hz, J=6.8 Hz, 2H); 4.24 (t, J=2.2 Hz, 2H).

$^{13}$C NMR (50 MHz, $CDCl_3$) δ ppm: 14.0, 18.5, 18.7, 22.6, 28.6, 28.8, 29.1, 29.2, 31.8, 51.4.

IR $cm^{-1}$: 722, 1009, 1138, 1329, 1378, 1460, 1673, 2236, 2855, 2925, 3332.

2.1.2. Compound I2: tridec-2-yn-1-ol

Yield: 75%

$^1$H NMR (200 MHz, $CDCl_3$) δ ppm: 0.88 (t, J=6.8 Hz, 3H); 1.26-1.55 (m, 14H); 2.20 (tt, J=2.2 Hz, J=6.8 Hz, 2H); 4.25 (t, J=2.2 Hz, 2H).

$^{13}$C NMR (50 MHz, $CDCl_3$) δ ppm: 14.1, 18.7, 22.6, 28.6, 28.8, 29.1, 29.3, 29.5, 29.6, 31.9, 51.4.

IR $cm^{-1}$: 721, 1011, 1137, 1227, 1377, 1565, 2228, 2853, 2922, 3335.

2.1.3. Compound I3: pentadec-2-yn-1-ol

Yield: 72%

$^1$H NMR (200 MHz, $CDCl_3$) δ ppm: 0.88 (t, J=6.2 Hz, 3H); 1.26-1.55 (m, 20H); 2.20 (tt, J=2.0 Hz, J=6.8 Hz, 2H); 4.25 (t, J=2.2 Hz, 2H).

$^{13}$C NMR (50 MHz, $CDCl_3$) δ ppm: 14.1, 18.7, 22.7, 28.6, 28.8, 29.1, 29.3, 29.5, 29.6, 31.9, 51.4.

IR $cm^{-1}$: 668, 749, 1007, 1136, 1215, 1380, 1466, 2855, 2926, 3335.

2.2. Step (2): Synthesis of alc-(n+9)-yn-1-ol J

General Procedure:

To 120 mmol NaH (6.3 eq, at 60%) washed three times with pentane under inert atmosphere of nitrogen are added by fractions 440 mmol (22 eq) of 1,3-diaminopropane distilled over calcium hydride. The mixture is heated at 70° C. for one hour and then the alkynol I (20 mmol, 1 eq) is added. The mixture is heated again at 70° C. for 6 h and then at 50° C. overnight and finally hydrolyzed and then extracted with ethyl acetate. The organic phase is washed three times with water and then with a 0.1M HCl solution, dried on $MgSO_4$, filtered and then evaporated under vacuum. Purification is carried out by filtration on a silica gel in successive mixtures of cyclohexane and ethyl acetate in proportions of 9:1, 8:2 and 7:3.

2.2.1. Compound J1: undec-10-yn-1-ol

Yield: 75%

$^1$H NMR (200 MHz, $CDCl_3$) δ ppm: 1.31-1.56 (m, 16H); 1.93 (t, J=2.4 Hz, 1H); 2.17 (td, J=2.4 Hz, J=6.8 Hz, 2H); 3.63 (t, J=6.4 Hz, 2H).

$^{13}$C NMR (50 MHz, $CDCl_3$) δ ppm: 18.3, 25.6, 28.4, 28.6, 28.9, 29.3, 29.4, 32.7, 63.0, 68.0, 84.6

IR $cm^{-1}$: 629, 667, 754, 1055, 1215, 1377, 1463, 1717, 2118, 2856, 2927, 3013, 3310.

2.2.2. Compound J2: tridec-12-yn-1-ol

Yield: 67%

$^1$H NMR (200 MHz, $CDCl_3$) δ ppm: 1.26-1.57 (m, 20H); 1.91 (t, J=2.6 Hz, 1H); 2.14 (td, J=2.6 Hz, J=6.8 Hz, 2H); 3.61 (t, J=6.6 Hz, 2H).

$^{13}$C NMR (50 MHz, $CDCl_3$) δ ppm: 18.3, 25.7, 28.4, 28.7, 29.0, 29.4, 32.7, 62.9, 67.9, 84.7.

IR $cm^{-1}$: 629, 667, 752, 1053, 1216, 1465, 2117, 2855, 2926, 3014, 3310.

2.2.3. Compound J3: pentadec-14-yn-1-ol

Yield: 97%

$^1$H NMR (200 MHz, $CDCl_3$) δ ppm: 1.25-1.62 (m, 24H); 1.91 (t, J=2.8 Hz, 1H); 2.16 (td, J=2.6 Hz, J=7.0 Hz, 2H); 3.61 (t, J=6.6 Hz, 2H).

$^{13}$C NMR (50 MHz, $CDCl_3$) δ ppm: 18.3, 25.7, 28.4, 28.5, 28.7, 29.1, 29.4, 32.7, 62.9, 67.9, 84.7.

IR $cm^{-1}$: 557, 631, 668, 749, 1050, 1215, 1465, 2856, 2928, 3015, 3308.

2.3. Step (3): Synthesis of Compounds K

General Procedure:

To a solution of alkyne J (5 mmol, 1 eq) and 2-chloroquinoline (6.5 mmol, 1.3 eq) in triethylamine (25 mmol, 5 eq) and THF (3 ml) under inert atmosphere of nitrogen are added PdCl$_2$(PPh$_3$)$_3$ (0.25 mmol, 0.05 eq) and CuI (0.5 mmol, 0.1 eq) in this order. The mixture is heated at 70° C. for 3 hours, hydrolyzed and extracted with dichloromethane. The organic phase is then washed with water and then with a 0.1M HCl solution, dried on MgSO$_4$, and then evaporated under reduced pressure. Purification is carried out on a silica column in a mixture of cyclohexane and ethyl acetate in a proportion of 7:3 and then 6:4. A secondary product resulting from the dimerization of the alkyne compound with itself is obtained with a yield between 10% and 20%.

2.3.1. Compound K1:
11-(quinolin-2-yl)undec-10-yn-1-ol

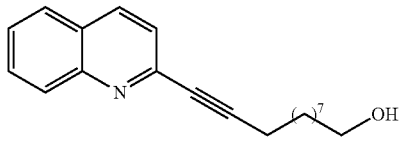

Yield: 87%

$^1$H NMR (400 MHz, CDCl$_3$) δ ppm: 1.32 (s, 8H); 1.46 (m, 2H); 1.55 (m, 2H); 1.64 (m, 2H); 2.48 (t, J=7.2 Hz, 2H); 3.62 (t, J=6.8 Hz, 2H); 7.43 (d, J=8.4 Hz, 1H); 7.49 (t, J=7.6 Hz, 1H); 7.68 (t, J=8.0 Hz, 1H); 7.75 (d, J=8.4 Hz, 1H); 8.06 (d, J=8.4 Hz, 2H).

$^{13}$C NMR (50 MHz, CDCl$_3$) δ ppm: 19.4, 25.6, 28.2, 28.8, 28.9, 29.2, 29.3, 32.7, 62.8, 81.1, 92.1, 124.1, 126.6, 126.8, 127.3, 129.0, 129.7, 135.8, 144.0, 147.9

MS (EI)-m/z: 295 (M$^+$, 2); 278 (C$_{20}$H$_{24}$N$_1$, 6); 264 (C$_{19}$H$_{22}$N$_1$, 13); 250 (C$_{18}$H$_{20}$N$_1$, 17); 236 (C$_{17}$H$_{18}$N$_1$, 34); 222 (C$_{16}$H$_{16}$N$_1$, 80); 208 (C$_{15}$H$_{14}$N$_1$, 76); 194 (C$_{14}$H$_{12}$N$_1$, 54); 180 (C$_{13}$H$_{10}$N$_1$, 100); 166 (C$_{12}$H$_8$N$_1$, 42); 140 (C$_{10}$H$_6$N$_1$, 38); 128 (C$_9$H$_6$N$_1$, 26).

IR cm$^{-1}$: 617, 637, 694, 721, 754, 787, 829, 871, 953, 1057, 1120, 1141, 1238, 1261, 1277, 1307, 1336, 1373, 1424, 1463, 1500, 1555, 1595, 1617, 2226, 2853, 2925, 3058, 3312.

2.3.2. Compound K2:
13-(quinolin-2-yl)tridec-12-yn-1-ol

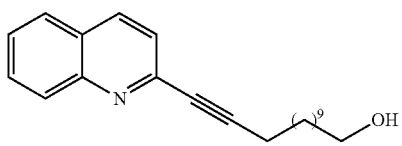

Yield: 76%

$^1$H NMR (400 MHz, CDCl$_3$) δ ppm: 1.28 (s, 14H); 1.49 (m, 2H); 1.55 (m, 2H); 1.66 (m, 2H); 2.48 (t, J=7.2 Hz, 2H); 3.62 (t, J=6.4 Hz, 2H); 7.43 (d, J=8.4 Hz, 1H); 7.49 (t, J=7.6 Hz, 1H); 7.68 (t, J=8.0 Hz, 1H); 7.75 (d, J=8.4 Hz, 1H); 8.05 (d, J=8.4 Hz, 1H).

$^{13}$C NMR (400 MHz, CDCl$_3$) δ ppm: 19.4, 25.6, 26.8, 28.9, 29.1, 29.3, 29.4, 29.5, 30.1, 32.7, 43.4, 62.9, 81.0, 92.1, 124.1, 126.6, 126.8, 127.3, 129.1, 129.8, 135.9, 144.1, 147.9.

MS (EI)-m/z: 323 (M$^+$, 1); 306 (C$_{22}$H$_{28}$N$_1$, 2); 292 (C$_{21}$H$_{26}$N$_1$, 3); 278 (C$_{20}$H$_{24}$N$_1$, 6); 264 (C$_{19}$H$_{22}$N$_1$, 11); 250 (C$_{18}$H$_{20}$N$_1$, 17); 236 (C$_{17}$H$_{18}$N$_1$, 35); 222 (C$_{16}$H$_{16}$N$_1$, 70); 208 (C$_{15}$H$_{14}$N$_1$, 56); 194 (C$_{14}$H$_{12}$N$_1$, 44); 180 (C$_{13}$H$_{10}$N$_1$, 100); 166 (C$_{12}$H$_8$N$_1$, 29); 140 (C$_{10}$H$_6$N$_1$, 26); 128 (C$_9$H$_6$N$_1$, 16).

IR cm$^{-1}$: 617, 638, 665, 679, 722, 753, 786, 829, 870, 952, 1056, 1120, 1142, 1237, 1261, 1277, 1307, 1373, 1424, 1463, 1500, 1555, 1595, 1617, 2226, 2852, 2923, 3337.

2.3.3. Compound K3:
15-(quinolin-2-yl)pentadec-14-yn-1-ol

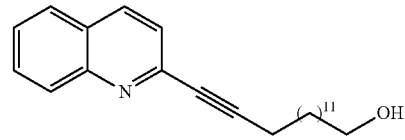

Yield: 44%

$^1$H NMR (400 MHz, CDCl$_3$) δ ppm: 1.26 (m, 18H); 1.42 (m, 2H); 1.49 (m, 2H); 1.61 (m, 2H); 2.48 (t, J=7.2 Hz, 2H); 3.62 (t, J=6.8 Hz, 2H); 7.44 (d, J=8.4 Hz, 1H); 7.49 (t, J=7.2 Hz, 1H); 7.68 (t, J=7.6 Hz, 1H); 7.75 (d, J=8.4 Hz, 1H); 8.06 (d, J=8.4 Hz, 2H).

$^{13}$C NMR (400 MHz, CDCl$_3$) δ ppm: 19.4, 25.7, 28.3, 28.9, 29.0, 29.2, 29.3, 29.4, 29.5, 29.6, 29.7, 31.2, 32.7, 38.1, 62.9, 76.6, 73.3, 81.0, 92.2, 124.1, 126.6, 126.8, 127.3, 129.1, 129.7, 135.9, 144.1, 148.0.

MS (EI)-m/z: 351 (M$^+$, 6); 334 (C$_{24}$H$_{32}$N$_1$, 4); 320 (C$_{23}$H$_{30}$N$_1$, 3); 306 (C$_{22}$H$_{28}$N$_1$, 2); 292 (C$_{21}$H$_{26}$N$_1$, 5); 278 (C$_{20}$H$_{24}$N$_1$, 12); 264 (C$_{19}$H$_{22}$N$_1$, 15); 250 (C$_{18}$H$_{20}$N$_1$, 20); 236 (C$_{17}$H$_{18}$N$_1$, 42); 222 (C$_{16}$H$_{16}$N$_1$, 78); 208 (C$_{15}$H$_{14}$N$_1$, 67); 194 (C$_{14}$H$_{12}$N$_1$, 51); 180 (C$_{13}$H$_{10}$N$_1$, 100); 166 (C$_{12}$H$_8$N$_1$, 35); 140 (C$_{10}$H$_6$N$_1$, 22); 128 (C$_9$H$_6$N$_1$, 15).

IR cm$^{-1}$: 617, 639, 664, 679, 723, 753, 786, 829, 871, 953, 1056, 1120, 1141, 1238, 1261, 1277, 1307, 1336, 1373, 1424, 1462, 1500, 1555, 1595, 1617, 2226, 1854, 2926, 3059, 3337.

2.4. Step (4): Synthesis of Compounds L

General Procedure:

To a solution of alkyne K (0.5 mmol, 1 eq) in absolute ethanol (1 ml) are added 40 mg of Pd/C (mass ~20%). The system is stirred overnight under a stream of hydrogen at room temperature. The reaction mixture is then hydrolyzed by several drops of water and then filtered on celite. The filtrate is then dried on MgSO$_4$ and then evaporated under vacuum. The reaction is quantitative.

2.4.1. Compound L1:
11-(quinolin-2-yl)undecan-1-ol

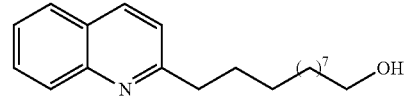

Yield: quantitative $^1$H NMR (400 MHz, CDCl$_3$) δ ppm: 1.26 (m, 14H); 1.55 (m, 2H); 1.80 (m, 2H); 2.96 (t, J=7.8 Hz, 2H); 3.63 (t, J=6.6 Hz, 2H); 7.29 (t, J=8.4 Hz, 1H); 7.47 (t, J=8.1 Hz, 1H); 7.67 (td, J=1.5 Hz, J=7.2 Hz, 1H); 7.76 (d, J=7.8 Hz, 1H); 8.05 (m, 2H).

$^{13}$C NMR (50 MHz, CDCl$_3$) δ ppm: 25.7, 29.4, 29.5, 29.5, 29.6, 30.1, 32.8, 39.3, 63.0, 77.2, 121.3, 125.6, 127.4, 128.7, 129.3, 136.2, 147.8, 163.1.

IR cm$^{-1}$: 623, 672, 725, 753, 775, 790, 834, 866, 894, 949, 974, 1013, 1054, 1124, 1210, 1321, 1381, 1427, 1461, 1504, 1567, 1601, 1619, 2848, 2919, 3055, 3253.

2.4.2. Compound L2: 13-(quinolin-2-yl)tridecan-1-ol

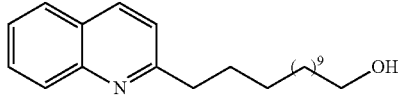

Yield: quantitative $^1$H NMR (400 MHz, CDCl$_3$) δ ppm: 1.25 (m, 18H); 1.54 (m, 3H); 1.80 (m, 2H); 2.96 (t, J=7.8 Hz, 2H); 3.64 (t, J=6.6 Hz, 2H); 7.30 (d, J=8.4 Hz, 1H); 7.48 (t, J=7.2 Hz, 1H); 7.68 (td, J=1.5 Hz, J=6.9 Hz, 1H); 7.77 (d, J=8.1 Hz, 1H); 8.05 (m, 2H).

$^{13}$C NMR (400 MHz, CDCl$_3$) δ ppm: 25.7, 29.4, 29.5, 30.1, 32.8, 39.4, 63.1, 77.2, 121.4, 125.6, 127.5, 128.8, 129.3, 136.2, 163.1.

MS (EI)-m/z: 328 ([M+H]$^+$, 100)

IR cm$^{-1}$: 623, 672, 725, 754, 777, 791, 835, 867, 903, 964, 1057, 1124, 1217, 1261, 1322, 1380, 1427, 1462, 1505, 1567, 1601, 1619, 2848, 2917, 3054, 3262.

2.4.3. Compound L3: 15-(quinolin-2-yl)pentadecan-1-ol

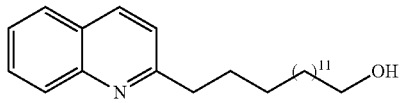

Yield: quantitative $^1$H NMR (400 MHz, CDCl$_3$)-δ ppm: 1.25 (m, 22H); 1.56 (m, 2H); 1.81 (m, 2H); 2.97 (t, J=7.8 Hz, 2H); 3.64 (t, J=6.6 Hz, 2H); 7.30 (d, J=8.7 Hz, 1H); 7.48 (t, J=7.8 Hz, 1H); 7.68 (td, J=1.5 Hz, J=6.3 Hz, 1H); 7.78 (d, J=7.8 Hz, 1H); 8.05 (m, 2H).

$^{13}$C NMR (400 MHz, CDCl$_3$) δ ppm: 25.7, 29.5, 30.1, 32.8, 39.3, 63.1, 121.4, 125.6, 126.7, 127.5, 128.7, 129.3, 126.3, 147.8, 163.1.

MS (EI)-m/z: 356 ([M+H]$^+$, 100)

IR cm$^{-1}$: 623, 672, 725, 744, 777, 791, 835, 867, 903, 964, 1057, 1124, 1215, 1261, 1322, 1380, 1427, 1462, 1505, 1567, 1601, 1619, 2325, 2848, 2917, 3054, 3263.

2.5. Steps (5) and (5a): Synthesis of Compounds M and M'

General Procedure:

To a solution of oxalyl chloride (0.624 mmol, 2.2 eq) dissolved in distilled dichloromethane (5 ml) placed at −60° C. under inert atmosphere of nitrogen is added slowly 1.65 mmol (5.8 eq) of dimethyl sulfoxide (DMSO). After 15 minutes, alcohol K or L (0.284 mmol, 1 eq) dissolved in distilled dichloromethane (3 ml) is added. The temperature is maintained between −60° C. and −50° C. for 2 hours and then triethylamine (2.84 mmol, 10 eq) is added. The mixture is stirred until room temperature is reached and then hydrolyzed and extracted with dichloromethane. The organic phase is then washed three times with water and then with a 0.1M HCl solution, dried on MgSO$_4$, filtered and evaporated under reduced pressure. The mixture is purified on a silica column in a mixture of cyclohexane and ethyl acetate in a proportion of 9:1.

2.5.1. Compound M1: 11-(quinolin-2-yl)undec-10-yn-1-al

Yield: 68%

$^1$H NMR (400 MHz, CDCl$_3$) δ ppm: 1.33 (m, 12H); 2.40 (t, J=6.8 Hz, 2H); 2.48 (t, J=6.8 Hz, 2H); 7.45 (d, J=8.4 Hz, 1H); 7.52 (t, J=7.6 Hz, 1H); 7.68 (t, J=7.2 Hz, 1H); 7.76 (d, J=8.0 Hz, 1H); 8.06 (d, J=8.4 Hz, 2H); 9.75 (s, 1H).

$^{13}$C NMR (100 MHz, CDCl$_3$) δ ppm: 19.4, 21.9, 28.1, 28.2, 28.6, 28.8, 28.9, 29.0, 29.1, 29.2, 29.6, 43.7, 81.0, 91.9, 123.9, 124.1, 126.6, 126.8, 127.3, 127.4, 129.0, 129.7, 135.9, 143.9, 147.9, 149.5, 202.7.

IR cm$^{-1}$: 625, 668, 745, 831, 909, 1215, 1425, 1463, 1501, 1555, 1596, 1722, 2227, 2856, 2929.

2.5.2. Compound M2: 13-(quinolin-2-yl)tridec-12-yn-1-al

Yield: 49%

$^1$H NMR (300 MHz, CDCl$_3$) δ ppm: 1.30-1.70 (m, 16H); 2.40 (td, J=1.8 Hz, J=7.2 Hz, 2H); 2.49 (t, J=7.2 Hz, 2H); 7.44 (dd, J=1.5, J=8.4 Hz, 1H); 7.49 (t, J=7.2 Hz, 1H); 7.68 (td, J=1.5 Hz, J=8.4 Hz, 1H); 7.75 (d, J=8.4 Hz, 1H); 8.06 (d, J=8.4 Hz, 2H); 9.75 (t, J=1.5 Hz, 1H).

$^{13}$C NMR (75 MHz, CDCl$_3$) δ ppm: 19.4, 22.0, 26.8, 28.3, 28.9, 29.1, 29.3, 29.4, 29.6, 30.1, 43.8, 81.1, 92.0, 124.1, 126.6, 126.9, 127.3, 129.1, 129.7, 135.7, 144.1, 148.0, 202.7.

IR cm$^{-1}$: 585, 669, 751, 909, 1215, 1464, 1723, 2850, 2918.

2.5.3. Compound M3: 15-(quinolin-2-yl)pentadec-14-yn-1-al

Yield: 82%

$^1$H NMR (200 MHz, CDCl$_3$) δ ppm: 1.26-1.75 (m, 20H); 2.39 (td, J=2.0 Hz, J=7.4 Hz, 2H); 2.49 (t, J=7.0 Hz, 2H); 7.45 (d, J=8.4 Hz, 1H); 7.50 (t, J=1.4 Hz, 1H); 7.67 (dd, J=1.2 Hz, J=8.4 Hz, 1H); 7.75 (d, J=8.4 Hz, 1H); 8.06 (d, J=8.2 Hz, 2H); 9.74 (t, J=1.6 Hz, 1H).

$^{13}$C NMR (50 MHz, CDCl$_3$) δ ppm: 19.5, 22.0, 24.7, 28.3, 28.9, 29.1, 29.4, 34.1, 43.8, 92.5, 124.2, 126.7, 126.9, 127.3, 128.9, 129.0, 129.8, 136.0, 144.0, 147.9, 193.7.

IR cm$^{-1}$: 557, 622, 649, 727, 831, 905, 1045, 1123, 1142, 1239, 1374, 1425, 1464, 1501, 1556, 1595, 1618, 1711, 2227, 2853, 2924.

2.5.4. Compound M'1: 11-(quinolin-2-yl)undecan-1-al

Yield: 50%

$^1$H NMR (400 MHz, CDCl$_3$) δ ppm: 1.27 (m, 13H); 1.65 (m, 3H); 1.77 (m, 2H); 2.39 (td, J=1.8 Hz, J=7.8 Hz, 2H); 2.97 (t, J=7.8 Hz, 2H); 7.29 (d, J=8.4 Hz, 1H); 7.47 (t, J=7.2 Hz, 1H); 7.67 (td, J=1.5 Hz, J=6.9 Hz, 1H); 7.76 (d, J=8.1 Hz, 1H); 8.05 (d, J=8.4 Hz, 1H); 9.74 (s, 1H).

$^{13}$C NMR (50 MHz, CDCl$_3$) δ ppm: 22.0, 28.6, 28.9, 29.1, 29.3, 29.5, 29.5, 298.7, 30.0, 30.1, 39.3, 43.9, 77.3, 121.4, 125.7, 128.3, 128.7, 136.6, 147.8, 163.1, 203.0.

IR cm$^{-1}$: 621, 665, 723, 756, 828, 870, 954, 1017, 1122, 1142, 1185, 1310, 1427, 1464, 1505, 1564, 1601, 1619, 1720, 2852, 2923.

2.5.5. Compound M'2: 13-(quinolin-2-yl)tridecan-1-al

Yield: 91%

$^{1}$H NMR (400 MHz, CDCl$_{3}$) δ ppm: 1.25 (m, 16H); 1.64 (m, 3H); 1.80 (m, 2H); 2.40 (td, J=1.8 Hz, J=7.2 Hz, 2H); 2.96 (t, J=7.8 Hz, 2H); 7.28 (d, J=8.4 Hz, 1H); 7.47 (t, J=7.2 Hz 1H); 7.67 (td, J=1.5 Hz, J=6.9 Hz, 1H); 7.77 (d, J=8.1 Hz, 1H); 8.04 (t, J=8.4 Hz, 1H); 9.75 (t, J=2.1 Hz, 1H).

$^{13}$C NMR (400 MHz, CDCl$_{3}$) δ ppm: 22.0, 26.9, 29.1, 29.3, 29.4, 29.5, 29.5, 30.0, 39.4, 43.9, 77.2, 121.3, 125.6, 126.7, 127.4, 128.8, 129.3, 136.2, 147.8, 163.1, 203.0.

IR cm$^{-1}$: 578, 619, 722, 756, 827, 955, 1017, 1117, 1142, 1184, 1310, 1427, 1464, 1505, 1563, 1601, 1619, 1722, 2852, 2922.

2.5.6. Compound M'3: 15-(quinolin-2-yl)pentadecan-1-al

Yield: 88%

$^{1}$H NMR (400 MHz, CDCl$_{3}$) δ ppm: 1.20 (m, 19H); 1.57 (m, 3H); 1.85 (m, 2H); 2.37 (td, J=1.8 Hz, J=7.2 Hz, 2H); 3.30 (t, J=7.8 Hz, 2H); 7.53 (d, J=8.7 Hz, 1H); 7.67 (t, J=7.2 Hz 1H); 7.86 (t, J=7.2 Hz, 1H); 7.96 (d, J=8.4 Hz, 1H); 8.67 (d, J=8.1 Hz, 1H); 8.70 (d, J=8.4 Hz, 1H); 9.72 (t, J=1.8 Hz, 1H).

$^{13}$C NMR (400 MHz, CDCl$_{3}$) δ ppm: 22.0, 28.6, 28.9, 29.1, 29.3, 29.5, 29.5, 298.7, 30.0, 30.1, 39.3, 43.9, 77.3, 121.4, 125.7, 128.3, 128.7, 136.6, 147.8, 163.1, 203.0.

IR cm$^{-1}$: 578, 619, 722, 756, 827, 955, 1017, 1117, 1142, 1184, 1310, 1427, 1464, 1505, 1563, 1601, 1619, 1722, 2852, 2922.

2.6. Steps (6) and (6a): Synthesis of Compounds N and N'

2.6.1. Case in which $R^{2a}$=—C≡CH

General Procedure:

(a) Preparation of the Lithium Solution

To a solution of trimethylsilylacetylene (0.7 ml, 5 mmol, 1 eq) in THF (5 ml), placed under inert atmosphere of nitrogen at −78° C., is added drop by drop 2.5 M n-butyllithium (2 ml, 5 mmol, 1 eq). The solution is stirred for 1 hour at −78° C.

(b) Coupling

A solution of aldehyde M or M' (0.2 mmol, 1 eq) in THF (5 ml) is placed at −78° C. under inert atmosphere of nitrogen and then 0.24 mmol (1.2 eq) of the lithium solution prepared beforehand is added. The solution is stirred at −78° C. for 2 hours. The reaction mixture is then hydrolyzed and extracted with dichloromethane. The organic phases are combined and dried on MgSO$_{4}$, filtered and then evaporated. The products obtained were not purified and were then desilylated.

(c) Deprotection of the Silylated Group

A solution of the silylated coupling product obtained in preceding step (b) (0.1 mmol, 1 eq) in THF (8 ml) is stirred under an inert atmosphere of nitrogen at room temperature. 0.106 mmol (1.06 eq) TBAF is then added. After 10 minutes, the reaction mixture is hydrolyzed and extracted with ethyl acetate. The combined organic phases are washed three times successively with saturated aqueous solutions of NaHCO$_{3}$ and NaCl, dried on MgSO$_{4}$, filtered and evaporated under reduced pressure. Purification is carried out on a silica column in a mixture of cyclohexane and ethyl acetate in a proportion of 9:1.

2.6.1.1. Compound N1: 13-(quinolin-2-yl)tridec-1,12-diyn-3-ol

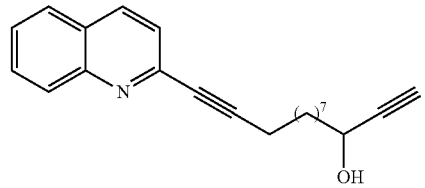

Yield: 72%

$^{1}$H NMR (400 MHz, CDCl$_{3}$) δ ppm: 1.25 (m, 19H); 1.45 (m, 3H); 1.69 (m, 2H); 2.44 (d, J=2.0 Hz, 1H); 2.49 (t, J=7.2 Hz, 2H); 4.37 (td, J=2.0 Hz, J=6.4 Hz, 1H); 7.45 (d, J=8.4 Hz, 1H); 7.51 (t, J=7.2 Hz, 1H); 7.69 (td, J=1.2 Hz, J=6.8 Hz, 1H); 7.76 (d, J=8.0 Hz, 1H); 8.07 (d, J=8.4 Hz, 2H).

$^{13}$C NMR (50 MHz, CDCl$_{3}$) δ ppm: 19.5, 25.0, 28.3, 29.0, 29.1, 29.2, 29.4, 29.5, 37.7, 62.4, 72.7, 81.1, 92.2, 115.1, 124.2, 126.7, 126.9, 127.4, 129.2, 129.8, 134.4, 136.0, 136.1, 148.1.

ESI-MS m/z: 320 ([M+H]$^{+}$, 100).

IR cm$^{-1}$: 626, 752, 786, 830, 871, 953, 1033, 1121, 1141, 1238, 1261, 1277, 1308, 1374, 1425, 1463, 1501, 1556, 1595, 1618, 2226, 2853, 2924, 3306.

2.6.1.2. Compound N2: 15-(quinolin-2-yl)pentadec-1,14-diyn-3-ol

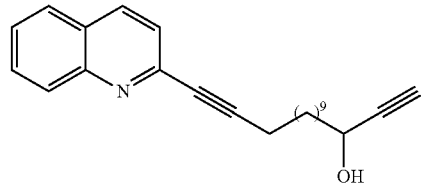

Yield: 92%

$^{1}$H NMR (400 MHz, CDCl$_{3}$) δ ppm: 1.25 (m, 14H); 1.50 (m, 3H); 1.70 (m, 2H); 2.44 (d, J=2.0 Hz, 1H); 2.49 (t, J=7.2 Hz, 2H); 4.37 (td, J=2.0 Hz, J=6.4 Hz, 1H); 7.45 (d, J=8.4 Hz, 1H); 7.51 (t, J=7.6 Hz, 1H); 7.69 (td, J=1.2 Hz, J=6.8 Hz, 1H); 7.76 (d, J=8.0 Hz, 1H); 8.07 (d, J=8.2 Hz, 2H).

$^{13}$C NMR (50 MHz, CDCl$_{3}$) δ ppm: 19.5, 25.0, 28.3, 29.0, 29.1, 29.2, 29.4, 29.5, 37.7, 62.4, 72.7, 81.1, 92.2, 115.1, 124.2, 126.7, 126.9, 127.4, 129.2, 129.8, 134.4, 136.0, 136.1, 148.1.

ESI-MS m/z: 348 ([M+H]$^{+}$, 100).

IR cm$^{-1}$: 54, 627, 665, 751, 830, 870, 1036, 1073, 1121, 1216, 1238, 1262, 1277, 1376, 1425, 1463, 1501, 1556, 1596, 1618, 1722, 2227, 2363, 2854, 2925, 3307.

2.6.1.3. Compound N3:
17-(quinolin-2-yl)heptadec-1,16-diyn-3-ol

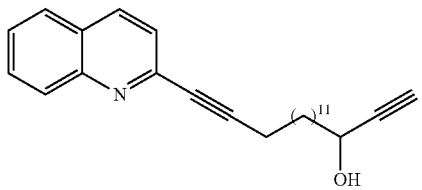

Yield: 74%

$^1$H NMR (400 MHz, CDCl$_3$) δ ppm: 1.25 (m, 10H); 1.67 (m,); 2.44 (d, J=2.0 Hz, 1H); 2.50 (t, J=7.2 Hz, 2H); 4.38 (td, J=1.6 Hz, J=6.8 Hz, 1H); 7.45 (d, J=8.4 Hz, 1H); 7.52 (t, J=7.6 Hz, 1H); 7.70 (t, J=7.2 Hz, 1H); 7.77 (d, J=8.0 Hz, 1H); 8.08 (d, J=8.0 Hz, 2H).

$^{13}$C NMR (50 MHz, CDCl$_3$) δ ppm: 19.5, 28.2, 28.8, 28.9, 29.0, 29.1, 29.2, 29.3, 37.6, 62.2, 122.3, 124.2, 126.8, 127.4, 129.0, 130.0.

ESI-MS m/z: 376 ([M+H]$^+$, 100).

IR cm$^{-1}$: 572, 627, 668, 746, 831, 929, 1049, 1214, 1425, 1501, 1596, 2231, 2361, 2401, 2856, 2928, 3019.

2.6.1.4. Compound N'1:
13-(quinolin-2-yl)tridec-1-yn-3-ol

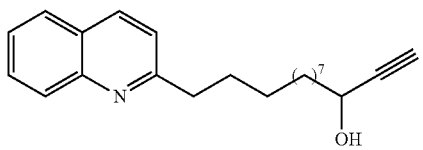

Yield: 84%

$^1$H NMR (400 MHz, CDCl$_3$) δ ppm: 1.24 (m, 16H); 1.44 (m, 2H); 1.70 (m, 3H); 2.42 (d, J=2.0 Hz, 1H); 2.76 (t, J=7.6 Hz, 2H); 4.39 (td, J=2.0 Hz, J=6.4 Hz, 1H); 7.49 (t, J=7.2 Hz, 1H); 7.62 (t, J=8.0 Hz, 1H); 7.74 (d, J=8.0 Hz, 1H); 8.09 (d, J=8.4 Hz, 2H); 8.76 (s, 1H).

$^{13}$C NMR (50 MHz, CDCl$_3$) δ ppm: 25.0, 29.1, 29.2, 29.3, 29.5, 31.0, 33.1, 37.7, 61.9, 72.3, 126.5, 127.2, 128.1, 128.6, 128.8, 134.3, 135.3, 146.4, 151.8.

ESI-MS m/z: 324 ([M+H]$^+$, 100).

IR cm$^{-1}$: 648, 721, 751, 787, 861, 907, 957, 986, 1047, 1128, 1330, 1379, 1465, 1498, 1575, 1716, 2021, 2160, 2341, 2360, 2852, 2922, 3308.

2.6.1.5. Compound N'2:
15-(quinolin-2-yl)pentadec-1-yn-3-ol

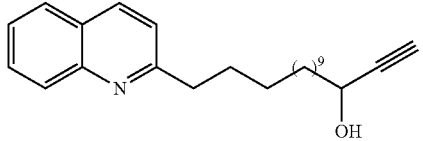

Yield: 50%

$^1$H NMR (400 MHz, CDCl$_3$) δ ppm: 1.25 (m, 20H); 1.70 (m, 2H); 1.80 (m, 2H); 2.44 (d, J=2.0 Hz, 1H); 2.83 (t, J=7.6 Hz, 2H); 4.38 (td, J=2.0 Hz, J=6.4 Hz, 1H); 7.52 (t, J=7.2 Hz, 1H); 7.66 (t, J=8.0 Hz, 1H); 7.76 (d, J=8.0 Hz, 1H); 8.11 (d, J=8.4 Hz, 2H); 8.79 (s, 1H).

$^{13}$C NMR (50 MHz, CDCl$_3$) δ ppm: 25.0, 29.1, 29.2, 29.4, 31.0, 33.1, 32.3, 37.7, 62.2, 72.6, 126.7, 127.3, 128.2, 128.6, 128.7, 134.7, 135.5, 146.1, 151.6.

ESI-MS m/z: 352 ([M+H]$^+$, 100).

IR cm$^{-1}$: 557, 621, 649, 722, 752, 786, 861, 907, 957, 986, 1019, 1129, 1232, 1265, 1330, 1464, 1498, 1577, 1713, 2852, 2922, 3308.

2.6.1.6. Compound N'3:
17-(quinolin-2-yl)heptadec-1-yn-3-ol

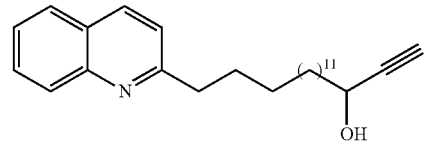

Yield: 50%

$^1$H NMR (300 MHz, CDCl$_3$) δ ppm: 1.26 (m, 18H); 1.75 (m, 4H); 2.97 (t, J=7.5 Hz, 1H); 4.37 (td, J=2.1 Hz, J=6.6 Hz, 1H); 7.30 (d, J=8.4 Hz, 1H); 7.48 (td, J=0.9 Hz, J=8.1 Hz, 1H); 7.68 (td, J=1.5 Hz, J=6.9 Hz, 1H); 7.77 (d, J=8.1 Hz, 1H); 8.07 (d, J=8.4 Hz, 1H).

$^{13}$C NMR (50 MHz, CDCl$_3$) δ ppm: 25.0, 26.9, 29.2, 29.5, 29.5, 30.0, 37.7, 39.3, 62.2, 72.7, 85.2, 121.4, 125.7, 126.7, 127.4, 128.7, 129.4, 136.3, 147.7, 163.1.

$^{13}$C ESI-MS m/z: 380 ([M+H]$^+$, 100).

IR cm$^{-1}$: 645, 723, 752, 784, 862, 909, 958, 1040, 1098, 1128, 1346, 1463, 1490, 1570, 1620, 2231, 2360, 2854, 2926, 3301.

2.6.2. Case in which R$^{2a}$=Vinyl or Cyclopropyl

General Procedure:

A solution of aldehyde M or M' (0.2 mmol, 1 eq) in THF (5 ml) is placed at −78° C. under inert atmosphere of nitrogen and then 0.24 mmol (1.2 eq) of a 2.5 M commercial solution of vinylmagnesium bromide or cyclopropylmagnesium bromide are added. The solution is stirred at −78° C. for 2 hours. The reaction mixture is then hydrolyzed and extracted with dichloromethane. The organic phases are combined and dried on MgSO$_4$, filtered and then evaporated.

2.6.2.1. Compound N4: 17-(quinolin-2-yl)heptadec-1-ene-16-yn-3-ol

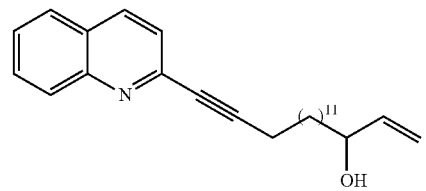

Yield: 81%

$^1$H NMR (300 MHz, CDCl$_3$) δ ppm: 1.27 (m, 14H); 1.50 (m, 5H); 1.67 (m, 3H); 2.49 (t, J=7.2 Hz, 2H); 4.09 (q, 6.0 Hz, 1H); 5.09 (d, J=10.5 Hz, 1H); 5.21 (d, J=17.1 Hz, 1H); 5.86 (td, 6.3 Hz, 3.9 Hz, 1H); 7.47 (d, 8.4 Hz, 1H); 7.51 (t, 7.2 Hz, 1H); 7.70 (t, 7.8 Hz, 1H); 7.77 (d, 8.1 Hz, 1H); 8.08 (d, 8.4 Hz, 2H).

$^{13}$C NMR (50 MHz, CDCl$_3$) δ ppm: 25.3, 26.9, 28.3, 29.0, 29.1, 29.5, 29.5, 37.0, 73.3, 77.2, 114.5, 124.2, 124.7, 125.9, 126.7, 127.4, 129.1, 129.9, 136.0, 141.3.

ESI-MS m/z: 378 ([M+H]$^+$, 100).

2.6.2.2. Compound N5: 16-(quinolin-2-yl)hexadec-1-cyclopropyl-15-yn-2-ol

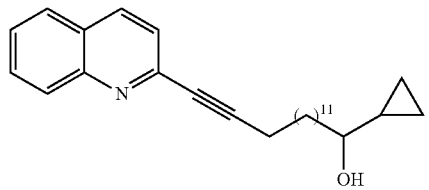

Yield: 41%

$^1$H NMR (300 MHz, CDCl$_3$) δ ppm: 0.22 (m, 2H); 0.49 (m, 2H); 0.88 (m, 1H); 1.27 (m, 14H); 1.49 (m, 4H); 1.63 (m, 5H); 2.49 (t, J=7.2 Hz, 2H); 2.84 (tdd, J=2.0 Hz, J=3.0 Hz, J=6.0 Hz, 1H); 7.45 (d, 8.4 Hz, 1H); 7.50 (t, 7.8 Hz, 1H); 7.69 (t, 7.8 Hz, 1H); 7.76 (d, 8.4 Hz, 1H); 8.07 (d, 8.4 Hz, 2H).

$^{13}$C NMR (50 MHz, CDCl$_3$) δ ppm: 2.4, 2.7, 18.0, 19.5, 25.7, 26.9, 28.3, 29.0, 29.1, 29.6, 29.7, 37.2, 81.0, 92.2, 124.2, 126.7, 126.9, 127.4, 129.1, 129.8, 135.9, 144.1, 148.0.

ESI-MS m/z: 392 ([M+H]$^+$, 100).

Example 2

Biological Tests 2.1. Experimental Protocols 2.1.1. Differentiating Activity on PC12 Pheochromocytoma Cells Maintenance.

The cells are maintained in 25 cm$^3$ flasks at 37° C. in a humid atmosphere enriched by 5% CO$_2$ in RPMI medium supplemented with 10% horse serum, 5% fetal calf serum, 1% glutamine and 1% penicillin/streptomycin mixture. The horse and fetal calf serums are decomplemented for 40 minutes at 56° C. before use. The cultures are divided when they reach 80% confluence, approximately every 3 days. Each operation is performed by scraping the cells and then centrifugation at 1,000 rpm for 5 minutes, mechanical dissociation of the cell aggregates and inoculation at the dilution desired.

Pretreatment.

Before treatment, the cells are cultivated 5 days in a deprivation medium composed of RPMI supplemented with 1% horse serum, 0.5% fetal calf serum, 1% glutamine, 1% penicillin/streptomycin and 50 ng/ml NGF (nerve growth factor).

Treatment.

After 5 days of pretreatment with NGF, the cells are washed twice with PBS (phosphate buffered saline), taken up in deprivation medium, scraped and pelleted at 1,000 rpm for 5 minutes. The cells are then dissociated, counted on a hemocytometer and inoculated at a concentration of $15.6 \times 10^3$ cells/cm$^2$. After 4 hours, the cells are treated by various compounds of the invention at the concentrations desired (stock solutions in absolute ethanol and then a series of dilutions in water).

Immunohistochemistry.

After 48 hours, the cells are fixed with a 4% formaldehyde solution and then washed three times with PBS. The cells then undergo anti-β$_{(III)}$-tubulin immunohistochemistry (tuj-1) visualized by a secondary antibody coupled to a fluorochrome that emits in the red spectrum (Cy3).

Image Analysis.

At least 20 differentiated cells per well are photographed at random and the length of their neurites are measured using the NeuronJ macro of the ImageJ software. The number of neurites is also counted. Mean total neurite length and number of neurites are then calculated per cell.

2.1.2. Neuroprotective Activity on Primary Culture of Rat Embryo Mesencephalon

Dissection.

Dissection consists in extracting the embryos from the uterus of a rat at fifteen days of gestation. The brain of each embryo is then dissected under a binocular magnifier in order to extract the ventral mesencephalon.

Inoculation.

The mesencephalons are gathered in a flask containing 2 ml of L15 medium and then mechanically dissociated (30 times), and then 5 ml of L15 medium are added. The suspension is left to rest for 8 minutes. 5 ml of the supernatant are recovered in a new flask and the cells are dissociated again (30 times). 5 ml of L15 are again added and the suspension is left to rest for 8 minutes. 5 ml of supernatant are added to the preceding. The cells thus extracted are then centrifuged for 5 minutes at 1,000 rpm. The cell pellet is taken up in Neurobasal medium supplemented with 1% B27, 1% glutamine and 1% penicillin/streptomycin mixture. The cells are then inoculated at the appropriate dilution (0.6 embryo per well on a 24-well plate and 0.4 per well on a 48-well plate). The cultures are incubated at 37° C. in a humid atmosphere enriched with 5% CO$_2$ in a 24- or 48-well plate.

Treatment.

After 24 hours, two-thirds of the medium of each well is replaced by new medium enriched with the compound of the invention to test at the appropriate dilution. The medium is replaced in the same way after 4 days of culture.

Immunohistochemistry.

At 8 days of culture, the cells are fixed by a 4% formaldehyde solution and then washed three times with PBS. The cells then undergo several immunohistochemistry procedures:

anti-tyrosine hydroxylase (TH) visualized by a secondary antibody coupled to a fluorochrome that emits in the red spectrum (Cy3).

anti-MAP2 (MAP=microtubule-associated protein) (neuron marker) visualized by a secondary antibody coupled to a fluorochrome that emits in the green spectrum (alexa488).

DAPI (4',6-diamidino-2-phenylindole), a nuclear marker that emits in the blue spectrum.

Analysis.

Neuroprotection is evaluated by counting TH positive neurons directly under the microscope or MAP2 positive on images, at 15 images per well, expressed as a percentage of the untreated control. The experiments include three wells per condition. Three independent experiments are carried out under these conditions. Total neurite length per cell calculated by the Neurite Outgrowth software by Explora Nova on 20 neurons photographed independently per well gives an indication of the state of maturation of the dopaminergic neurons.

2.1.3. Measurement of Dopamine Reuptake

Incorporation of Tritiated Dopamine.

The primary cultures are treated and cultivated as previously indicated for 12 days in a 24-well plate. The medium is then replaced by a medium lacking serum and enriched with glucose (PBS+5 mM glucose). One well is treated with GBR (5 µM) and will be used to determine nonspecific reuptake. The cells are incubated in this medium for 10 minutes. 50 µl of tritiated dopamine in solution (20 µl of 1 mCi/ml $^3$H-dopamine in 1 ml PBS) is added in each well and the cells are incubated for 20 minutes at 37° C.

Extraction of Intraneuronal Tritiated Dopamine.

The wells are then washed twice with PBS, and then 500 µl distilled water is added. The cells are scraped and the liquid transferred to scintillation vials containing 7 ml scintillation liquid (Biodegradable Counting Scintillant-liquid scintillation spectroscopy, BCS), well by well. The samples are run through the scintillation counter.

2.1.4. Measurement of GABA Reuptake

Incorporation of Tritiated GABA (Gamma-Aminobutyric Acid).

The primary cultures are treated and cultivated as previously indicated with 0.5 embryo per well in a 24-well plate for 12 days. The medium is then replaced by a medium lacking serum and enriched with glucose (PBS+5 mM glucose). The cells are incubated in this medium for 10 minutes. 50 µl of tritiated GABA in solution (20 µl of 1 mCi/ml $^3$H-GABA in 1 ml PBS) is added in each well and the cells are incubated for 5 minutes at 37° C. Since GABA is taken back up very quickly, it is important to be fast when adding reagents and not to handle too many wells at the same time.

Extraction of Intraneuronal Tritiated GABA.

All wells except one are then washed twice with PBS, and then 500 µl distilled water is added. The cells are scraped and the liquid transferred to scintillation vials containing 7 ml scintillation liquid (Biodegradable Counting Scintillant-liquid scintillation spectroscopy, BCS), well by well. The plate containing the remaining well is placed on ice for 30 minutes, then 50 µl of the same GABA solution is added. After 5 minutes, the well is washed twice with PBS and then the cells are lysed with 500 µl distilled water, scraped and the liquid is transferred to a vial containing 5 ml scintillation liquid. This well will be used to measure non-specificity. The samples are run through the scintillation counter.

2.2. Biological Results Obtained

2.2.1. Effects of the Compounds of the Invention on Differentiation of the PC12 Pheochromocytoma Line The neuritogenesis of PC12 cells starts 24 hours after treatment and reaches a maximum after 48 hours. In order to quantify the differentiation of PC12 cells we calculated the ratio between the number of cells emitting dendritic extensions and the total number of cells 48 hours after treatment with our substances at 100 nM and at 1 µM. Morphological changes at the microscopic level were quantified for the cells emitting extensions at approximately 100 cells per condition. Thus number of neurites and mean neurite length per cell were measured using the NeuronJ measurement software by ImageJ.

As indicated in FIG. 1A, two to three times as many cells produce extensions after treatment with compounds N1, N2 and N3 by comparison with untreated cells, thus showing an increase in the percentage of cell differentiation with the compounds of the invention. NGF (neurotrophic growth factor) is used as a positive control in the experiment. In addition, between 100 nM and 1 µM, it does not seem to have a dose-dependent effect.

Figure 1B:
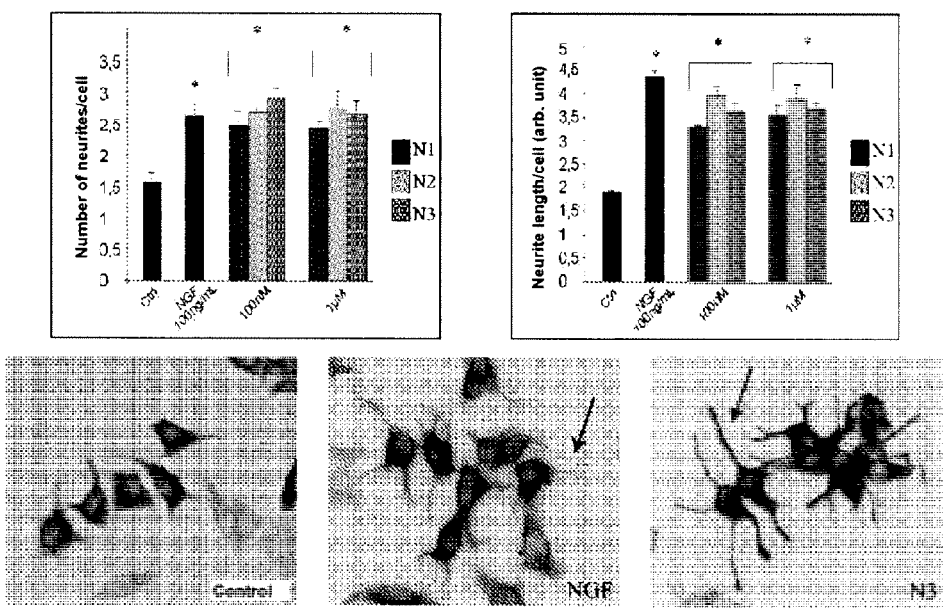
FIG. 1B relates to two graphs representing, respectively, the number of neurites per cell and neurite length per cell for the control, NGF (100 ng/ml) and for N1, N2 and N3 (100 nM and 1 μM), this study having been carried out on PC12 cells. Three photographs also show the control cells and those obtained after treatment with NGF or N3 (100 nM), clearly showing the effect of N3 on cell neurites.

In addition, the degree of differentiation comprising the number of neurites per cell as well as the mean neurite length per cell was measured showing neurons bearing more and longer extensions after treatment with N1, N2 and N3, compared to the control (see FIG. 1B).

2.2.2. Effects of the Compounds of the Invention on Neuroprotection and Differentiation of Dopaminergic Neurons in Primary Culture in a Model of Spontaneous Degeneration The compounds of the invention were tested on a model of spontaneous degeneration of dopaminergic neurons in culture.

This model consists of culturing cells of the ventral mesencephalon of rat embryo. This part of the brain in culture contains dopaminergic neurons and other primarily GABAergic neurons. These cultures are also composed of glial cells, namely astrocytes, oligodendrocytes and microglia. This is a model of spontaneous degeneration of dopaminergic neurons which mimics certain aspects of Parkinson's disease.

The neuroprotective effect of the compounds of the invention was evaluated by counting dopaminergic neurons (TH$^+$) marked by tyrosine hydroxylase (TH) immunohistochemistry after 8 days of culture. Thus the compounds were evaluated at 1 nM, 10 nM, 100 nM and 1 µM and were compared with the activity of dibutyryl cyclic AMP (db-cAMP) used as the reference product.

The results obtained are indicated in Table 1 below.

TABLE 1

Activity of compounds of the invention at 100 nM on survival of fetal dopaminergic neurons in culture.

| Compound of the invention | % Neurons relative to the control ±SEM[a] | Diff[b] |
| --- | --- | --- |
| control | 100 ± 2.7% | + |
| db-cAMP | 149.9 ± 3.6% | +++ |
| N1 | 127.2 ± 4.1% | ++ |
| N2 | 141.4 ± 4.1% | +++ |
| N3 | 154.5 ± 4.1% | +++ |
| Z1 | 98.2 ± 6.3% | − |
| N1 | 115.8 ± 3.9% | ++ |
| N2 | 129.6 ± 5.3% | +++ |
| N3 | 142.6 ± 2.6% | +++ |
| Z2 | 117.6 ± 6.1% | + |
| K2 | 121.4 ± 3.1% | ++ |
| Z3 | 103.9 ± 4.2% | − |
| F1 | 124.8 ± 5.5% | +++ |
| F2 | 120.2 ± 3.1% | +++ |
| F3 | 113.5 ± 3.8% | ++ |
| F4 | 101.2 ± 2.2% | ++ |
| F5 | 118.8 ± 0.7% | ++ |
| G1 | 131.1 ± 10.9% | +++ |
| G2 | 135.3 ± 4.4% | +++ |
| G3 | 113.1 ± 7.0% | ++ |
| G4 | 111.4 ± 5.3% | ++ |
| G5 | 130.4 ± 7.0% | ++ |

[a]Standard error of the mean.
[b]Diff is a qualitative assessment of neuron differentiation:
+ indicates that the neurons have a morphology similar to that of the control,
++ and +++ indicate the presence of neurons whose extensions are longer and more numerous than the control neurons,
− indicates that the neurons have neurites that are shorter and less numerous than the control neurons.
Note: Compounds Z1, Z2 and Z3 have the following chemical formulas:

TABLE 1-continued

Activity of compounds of the invention at 100 nM on survival of fetal dopaminergic neurons in culture.

| Compound of the invention | % Neurons relative to the control ±SEM[a] | Diff[b] |
|---|---|---|
| Z1 | | |
| Z2 | | |
| Z3 | | |

They differ from the compounds of the invention only by the position of the aliphatic chain on the quinoline nucleus (position 3 as opposed to position 2 for the quinoline derivatives of the invention). These compounds were synthesized according to the same experimental protocol as for the quinoline compounds of the invention, except that 3-bromoquinoline was used as starting product.

Quinoline Derivatives of the Invention:

An increase in neuroprotective activity is observed with all of the quinoline compounds of the invention, and it is particularly strong for compounds N2 and N3 and N'3 (compounds with a longer aliphatic chain) with a percentage of survival equal to or greater than that of the reference product.

In addition, the importance of the position of the aliphatic chain on the quinoline nucleus can be noted because compounds substituted at position 3 have much weaker activity or no activity at all.

Figure 2:
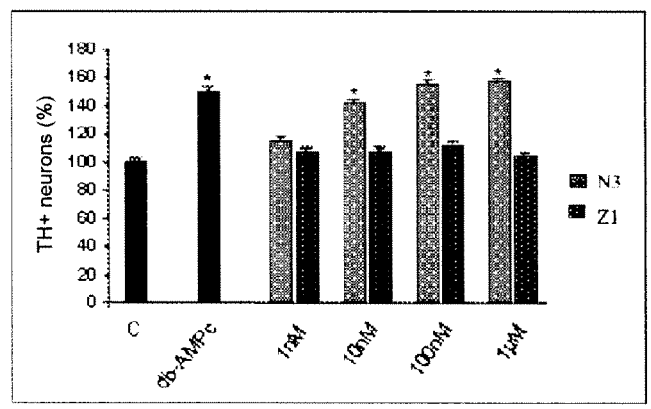
FIG. 2 represents the dose-response curve for compounds N3 and Z1 on the survival of dopaminergic neurons.

The dose-response curve for compounds N3 and Z1 on survival of dopaminergic neurons is presented in FIG. 2 and shows that the effect of compound N3 is dose-dependent and appears to have a maximum at 100 nM whereas the effect of compound Z1 is zero at all the concentrations tested. The data are expressed as a percentage of the negative control.

In order to evaluate more quantitatively the activity of the compounds of the invention, neurite growth per cell was measured using the Neurite Outgrowth software developed by Explora Nova. A minimum of 60 neurons per condition were photographed and studied, and the results were then averaged and normalized by the number of neurons considered.

Figure 3:
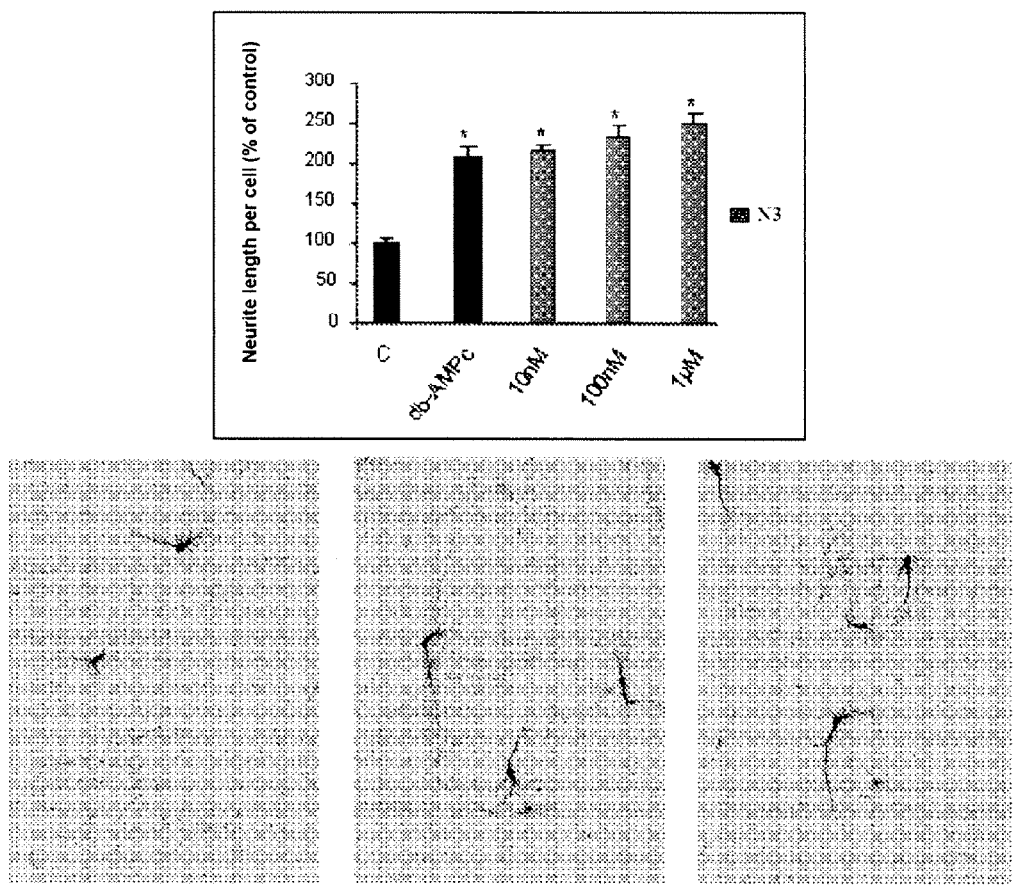
FIG. 3 represents neurite length per cell for the control, db-cAMP (200 μM) and for N3 (10 nM, 100 nM and 1 μM). Three photographs A, B and C represent untreated TH$^+$ neuron controls, TH$^+$ neurons treated with db-cAMP (200 μM) and TH$^+$ neurons treated with N3 (100 nM), respectively.

The compounds active on survival of dopaminergic neurons also showed activity on their differentiation with neurons having longer and more numerous dendritic extensions. The results obtained with compound N3 are presented in FIG. 3.

In order to confirm these results and to verify that the dopaminergic neurons treated remain functional, the capacity of dopaminergic neurons to reuptake dopamine was measured. Neurons at 12 days of culture are then cultivated for a short time in the presence of tritiated dopamine ($H^3$-DA). After washing, the cells are lysed and intraneuronal $H^3$-DA is recovered and assayed by scintillation counter.

The results obtained with compound N3 are presented in FIG. 4 (data expressed as a percentage of the value of the untreated control). They clearly show that the reuptake of dopamine by dopaminergic neurons is increased in the treated wells. This indicates that neuronal functionality is preserved during the treatment and confirms the results obtained previously.

Quinoxaline Derivatives of the Invention:

The quinoxaline derivatives of the invention thus exhibit good activity on neuronal differentiation.

It should also be noted that the activity of these compounds on the survival of dopaminergic neurons is better with an amine function than with an amide function and when the quinoxaline nucleus is not substituted at position 3, i.e. $R^3$=H.

2.2.3. Phenotypic Specificity of the Compounds of the Invention

In order to determine the possible specificity of the compounds of the invention, we continued our study with compound N3, the most active compound.

This study involved the other most represented neurons of the culture, namely GABAergic neurons, in order to determine if compound N3 has a specific action on dopaminergic neurons.

First, the neurons are cultured and maintained at DIV12. The cultures are fixed and then marked by immunohistochemistry against neuronal protein MAP2. The neurons are then counted via image with X20 enlargement at 15 images per well.

Second, in order to confirm these results, GABA reuptake by GABAergic neurons was measured by incorporation of tritiated GABA in the cultures.

The results obtained are presented in FIGS. 5 and 6 (data expressed as a percentage of the value of the untreated control). They show that survival and activity of total neurons of the culture are increased. The activity of compound N3 is thus not specific to dopaminergic neurons in this model.

Antimitotics, whose mechanism of action involves repression of astrocyte proliferation, also have a protective capacity in this model. Since the mechanism of action of our compounds is unknown, antimitotic activity is not excluded, thus making our compounds potentially effective against cancer.

The invention claimed is:

1. A compound of formula (I) as follows:

$$HetAr—X—CHR^1R^2 \quad (I)$$

wherein:

HetAr represents

X represents a linear, saturated or unsaturated hydrocarbon chain of from 8 to 22 carbon atoms optionally interrupted by an —NH— or —NH—CO— group, $R^1$ represents an $OR^5$ group, with $R^5$ representing a hydrogen atom or an $R^{5a}$ group selected from ($C_1$-$C_6$)alkyl, —CO(($C_1$-$C_6$)alkyl), —SO$_2$(($C_1$-$C_6$)alkyl) and —SO$_3$H, and R² represents an R²ᵃ group selected from a (C₂-C₆)alkynyl, (C₂-C₆)alkenyl or (C₃-C₆)cycloalkyl group, or a pharmaceutically acceptable salt or stereoisomer thereof.

2. The compound according to claim 1, wherein X represents a linear, saturated or unsaturated hydrocarbon chain having from 10 to 16 carbon atoms and optionally interrupted by an —NH— or —NH—CO— group.

3. The compound according to claim 1, wherein the —NH— or —NH—CO— group of X is directly linked to HetAr.

4. The compound according to claim 1, wherein the (C₂-C₆)alkynyl group is —C≡CH, the (C₂-C₆)alkenyl is —CH=CH₂, and the (C₃-C₆)cycloalkyl group is cyclopropyl.

5. The compound according to claim 1, wherein R² represents —C≡CH, —CH=CH₂ or cyclopropyl.

6. The compound according to claim 1, wherein R¹ represents an OH group and R² represents —C≡CH, —CH=CH₂ or cyclopropyl.

7. The compound according to claim 1, wherein R¹ represents an OH group.

8. The compound according to claim 7, wherein R² represents a —C≡CH group.

9. The compound according to claim 1, wherein X represents an X1 chain which is:
a saturated linear hydrocarbon chain; or
an unsaturated linear hydrocarbon chain comprising at least one triple bond or one double bond directly linked to HetAr.

10. The compound according to claim 1, wherein the X1 chain comprises from 10 to 16 carbon atoms.

11. The compound according to claim 1 selected from:

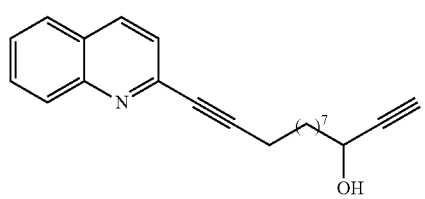
N1

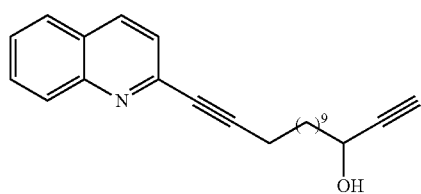
N2

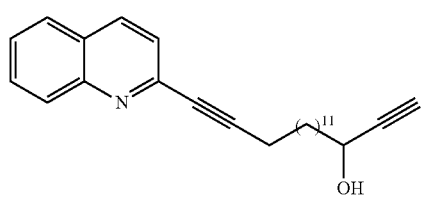
N3

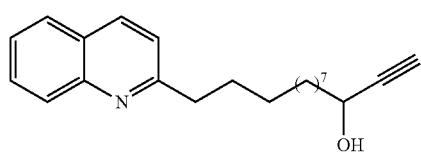
N'1

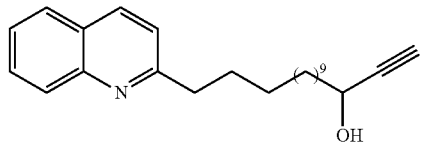
N'2

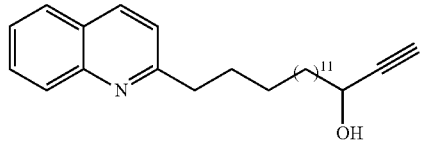
N'3

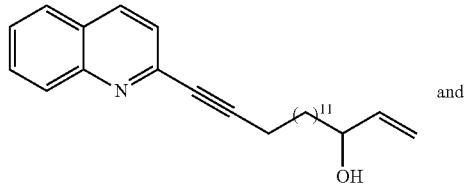
N4
and

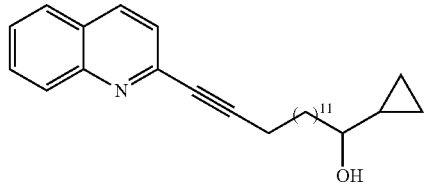
N5

12. A pharmaceutical composition comprising at least one compound according to claim 1 and one pharmaceutically acceptable carrier.

13. A method for preparing a compound of formula (I) according to claim 1, comprising the following steps:

oxidizing the alcohol function of a compound of formula (IV) as follows:

HetAr—X—CH₂(OH)     (IV)

to obtain a compound of formula (II) as follows:

HetAr—X—CHO     (II)

wherein HetAr represents

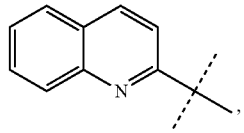
, and X represents a linear, saturated or unsaturated hydrocarbon chain of from 8 to 22 carbon atoms optionally interrupted by an —NH— or —NH—CO— group;

bringing together the compound of formula (II) with a compound of formula R²ᵇ-M, wherein R²ᵇ represents an R²ᵃ group, optionally in a protected form when R²ᵃ is —C≡CH, wherein the protected form is —C≡C—SiRᵃRᵇRᶜ, wherein Rᵃ, Rᵇ and Rᶜ independently represent (C₁-C₆)alkyl, and M represents an alkaline metal or an alkaline-earth metal linked to a halogen atom, to yield a compound of formula (III) as follows:

HetAr—X—CH(OH)R²ᵇ     (III)

optionally a step of deprotection of the $R^{2b}$ group to yield the $R^{2a}$ group in deprotected form, leading to a compound of formula (Ia) as follows:

HetAr—X—CH(OH)$R^{2a}$ (Ia)

optionally a step of substitution of the OH group of the compound of formula (Ia) obtained in the preceding step to yield a compound of formula (Ib) as follows:

HetAr—X—CH(OR$^{5a}$)$R^{2a}$ (Ib)

and recovery of compound (I) obtained in the preceding step and corresponding to compound (III), (Ia) or (Ib).

14. A method for preparing a compound of formula (I) according to claim 1, wherein X represents an —NH—CO—X2- group where NH is directly linked to HetAr and X2 represents a linear, saturated or unsaturated hydrocarbon chain, having from 8 to 22 carbon atoms, wherein said method comprises the following steps:

peptide coupling of a compound of formula (VII) as follows:

HetAr—NH$_2$ (VII), with a compound of formula (VIII) as follows:

Z—X2-CHR$^1$R$^2$ (VIII), wherein Z represents a carboxylic acid function optionally in activated form, wherein the activated form is —COCl, to yield the compound of formula (Ic) as follows:

HetAr—NHCO—X2-CHR$^1$R$^2$ (Ic), and recovery of compound (I) corresponding to compound (Ic) obtained in the preceding step.

15. A method for preparing a compound of formula (I) according to claim 1, comprising the following steps:

bringing together a compound of formula (II) as follows:

HetAr—X—CHO (II)

with a compound of formula $R^{2b}$-M, wherein $R^{2b}$ represents an $R^{2a}$ group, optionally in a protected form when $R^{2a}$ is —C≡CH, wherein the protected form is —C≡C—SiR$^a$R$^b$R$^c$, wherein R$^a$, R$^b$ and R$^c$ independently represent (C$_1$-C$_6$)alkyl, and M represents an alkaline metal or an alkaline-earth metal linked to a halogen atom, to yield a compound of formula (III) as follows:

HetAr—X—CH(OH)$R^{2b}$ (III)

optionally a step of deprotection of the $R^{2b}$ group to yield the $R^{2a}$ group in deprotected form, leading to a compound of formula (Ia) as follows:

HetAr—X—CH(OH)$R^{2a}$ (Ia)

optionally a step of substitution of the OH group of the compound of formula (Ia) obtained in the preceding step to yield a compound of formula (Ib) as follows:

HetAr—X—CH(OR$^{5a}$)$R^{2a}$ (Ib)

and recovery of compound (I) obtained in the preceding step and corresponding to compound (III), (Ia) or (Ib).

16. The method according to claim 15, wherein M represents lithium, bromo magnesium or chloro magnesium.

17. A method for preparing a compound of formula (I) according to claim 1, wherein X represents an —NH—CH$_2$—X3- group where X3 represents a linear, saturated or unsaturated hydrocarbon chain, comprising from 7 to 19 carbon atoms, wherein said method comprises the following steps:

peptide coupling of a compound of formula (VII) as follows:

HetAr—NH$_2$ (VII), with a compound of formula (IX) as follows:

Z—X3-CHR$^1$R$^2$ (IX), wherein Z represents a carboxylic acid function optionally in activated form, wherein the activated form is —COCl, to yield the compound of formula (X) as follows:

HetAr—NHCO—X3-CHR$^1$R$^2$ (X), reduction of the amide function to amine to yield the compound of formula (Id) as follows:

HetAr—NH—CH$_2$—X3-CHR$^1$R$^2$ (Id), and recovery of compound (I) corresponding to compound (Id) obtained in the preceding step.

18. The method according to claim 17, wherein the X3 chain comprises from 9 to 15 carbon atoms.

19. A method for preparing a compound of formula (I) according to claim 9, comprising the following steps:

Sonogashira coupling between a compound of formula (V) as follows:

HetAr-Hal (V), wherein Hal represents a chlorine or bromine atom, and a compound of formula (VI) as follows:

R$^2$R$^1$CH—X1-H (VI), optionally hydrogenation of the triple bond of the compound obtained in the preceding step of Sonogashira coupling, and recovery of the compound of formula (I) obtained in the preceding step.

20. The method according to claim 19, wherein R$^1$ represents an OH group.

* * * * *